US007117095B2

(12) United States Patent
Hubbell

(10) Patent No.: US 7,117,095 B2
(45) Date of Patent: Oct. 3, 2006

(54) METHODS FOR SELECTING NUCLEIC ACID PROBES

(75) Inventor: Earl Hubbell, Los Angeles, CA (US)

(73) Assignee: Affymetrix, Inc., Santa Clara, CA (US)

( * ) Notice: Subject to any disclaimer, the term of this patent is extended or adjusted under 35 U.S.C. 154(b) by 650 days.

(21) Appl. No.: 09/745,965

(22) Filed: Dec. 21, 2000

(65) Prior Publication Data

US 2002/0133301 A1   Sep. 19, 2002

Related U.S. Application Data

(60) Provisional application No. 60/252,617, filed on Nov. 21, 2000.

(51) Int. Cl.
*G01N 33/48* (2006.01)
*C12Q 1/68* (2006.01)
*C06F 7/00* (2006.01)

(52) U.S. Cl. .............................. 702/19; 702/20; 435/6; 707/102; 536/23.1

(58) Field of Classification Search ............ 702/19–29; 435/6; 536/23.1; 707/102
See application file for complete search history.

(56) References Cited

U.S. PATENT DOCUMENTS

| | | | |
|---|---|---|---|
| 5,571,639 A | 11/1996 | Hubbell et al. ................ | 430/5 |
| 5,593,839 A | 1/1997 | Hubbell et al. ................ | 435/6 |
| 5,800,992 A | 9/1998 | Fodor et al. .................... | 435/6 |
| 5,837,832 A | 11/1998 | Chee et al. | |
| 5,856,101 A | 1/1999 | Hubbell et al. ................ | 435/6 |
| 5,862,242 A | 1/1999 | Takewa et al. .............. | 381/398 |
| 5,871,928 A | 2/1999 | Fodor et al. .................... | 435/6 |
| 5,959,098 A | 9/1999 | Goldberg et al. | |
| 6,013,449 A | 1/2000 | Hacia et al. .................... | 435/6 |
| 6,027,880 A | 2/2000 | Cronin et al. .................. | 435/6 |
| 6,027,884 A | 2/2000 | Lane et al. ..................... | 435/6 |
| 6,040,138 A | 3/2000 | Lockhart et al. ............... | 435/6 |
| 6,040,183 A | 3/2000 | Ferrari et al. ............... | 435/457 |
| 6,130,046 A | 10/2000 | Hubbell et al. | |
| 6,153,743 A | 11/2000 | Hubbell et al. | |
| 6,188,783 B1 | 2/2001 | Balaban et al. | |
| 6,251,588 B1 * | 6/2001 | Shannon et al. ................ | 435/6 |
| 6,307,042 B1 | 10/2001 | Goldberg et al. | |
| 6,309,823 B1 | 10/2001 | Cronin et al. | |
| 6,340,565 B1 | 1/2002 | Oliner et al. | |
| 6,458,530 B1 | 10/2002 | Morris et al. | |
| 6,468,744 B1 | 10/2002 | Cronin et al. | |
| 6,706,875 B1 | 3/2004 | Goldberg et al. | |
| 6,746,844 B1 | 6/2004 | Oliner et al. | |
| 6,826,296 B1 | 11/2004 | Balaban et al. | |
| 2002/0102564 A1 | 8/2002 | Mittmann et al. | |

OTHER PUBLICATIONS

Mei, G. et al. Octamer-primed sequencing technology: development of primer identification software. Nucleic Acids Research (Apr. 1, 2000) vol. 28 No. 7 pp. e22 (i-ix).*

Burke et al., "A Validated Method for Clustering EST and Full-Length cDNA Sequences", *Genome Research*, vol. 9, 1999, pp. 1135-1142.

Chee et al., "Accessing Genetic Information with High-Density DNA Arrays", *Science*, abstract, vol. 274, Jul. 1996, 14 pages.

Cronin et al., "Cystic Fibrosis Mutation Detection by Hybridization to Light-Generated DNA Probe Arrays", *Human Mutation*, vol. 7, 1996, pp. 244-255.

de Saizieu et al., "Bacteria transcript imaging by hybridization of total RNA to oligonucleotide arrays", *Nature Biotechnology*, vol. 16, No. 1, Jan. 1998, pp. 45-48.

Hacia et al., "Strategies of Mutational Analysis of the Large Multiexon ATM Gene Using High-Density Oligonucleotide Arrays", *Genome Research*, vol. 8, Issue 12, Dec. 1998; pp. 1245-1258.

Hacia et al., "Detection of heterozygous mutations in BRCA1 using high density oligonucleotide arrays and two-color fluorescence analysis", *Nature Genetics*, vol. 14, 1996, pp. 441-447.

Hacia et al., "New approaches to BRCA1 mutation detection", *Breast Disease*, vol. 10, pp. 45-59.

Kozal et al., "Extensive polymorphisms observed in HIV-1 clade B protease gene using high density oligonucleotide arrays", *Nature Medicine*, vol. 2, No. 7, Jul. 1996, pp. 753-759.

Lockhart et al., "Expression monitoring by hybridization to high-density oligonucleotide arrays", *Nature Biotechnology*, vol. 14, Dec. 1996, pp. 1675-1680.

Lander "Array of Hope", *Nature-Genetics* vol. 21, 1999.

Searls, "Bioinformatics Tools for Whole Genomex", *Annu. Rev. Genom. Hum. Genetics*, vol. 1, 2000, pp. 251-279.

Ramsay, "DNA chips: State-of-Art", *Nature Biotechnology*, vol. 16, 1998, pp. 40-44.

Wodicka et al., "Genome-wide Expression Monitoring in *Saccharomyces cerevisiae*", *Nature Biotechnology*, vol. 15, Dec. 1997, pp. 1359-1367.

U.S. Appl. No. 09/721,042, filed Nov. 21, 2000, Hunt.
U.S. Appl. No. 09/718,295, filed Nov. 21, 2000, Mei.
U.S. Appl. No. 08/767,892, filed Dec. 17, 1996, Hubbell, et al.
U.S. Appl. No. 09/567,548, filed May 5, 2000, Hubbel, et al.
U.S. Appl. No. 09/607,536, filed Jun. 29, 2000, Hubbell, et al.
U.S. Appl. No. 10/975,245, filed Oct. 27, 2004, Hubbell, et al.
U.S. Appl. No. 09/811,364, filed Mar. 16, 2001, Balaban, et al.
U.S. Appl. No. 10/925,393, filed Aug. 24, 2004, Balaban, et al.
U.S. Appl. No. 09/640,962, filed Aug. 16, 2000, Hubbell.
U.S. Appl. No. 10/627,271, filed Jul. 25, 2003, Hubbell.
U.S. Appl. No. 11/038,614, filed Jan. 18, 2005, Hubbell, et al.
U.S. Appl. No. 10/226,355, filed Aug. 23, 2002, Morris, et al.
U.S. Appl. No. 10/017,034, filed Dec. 14, 2001, Mei, et al.
U.S. Appl. No. 10/308,379, filed Dec. 2, 2002, Mei.
U.S. Appl. No. 10/914,937, filed Aug. 9, 2004, Mei, et al.
U.S. Appl. No. 10/782,614, filed Feb. 19, 2004, Bekiranov, et al.

(Continued)

*Primary Examiner*—Mary K. Zeman
(74) *Attorney, Agent, or Firm*—Wei Zhou

(57) ABSTRACT

Methods and computer software products are provided for selecting nucleic acid probes. In one embodiment, dynamic programming is employed to select a set of k probes from n probes so that the selected probes have a maximum aggregate adjusted quality score.

27 Claims, 30 Drawing Sheets

OTHER PUBLICATIONS

Cheng, et al; NetAffx Gene Ontology Mining Tool: a visual approach for microarray data analysis; Bioinformatics Applications note; vol. 20; No. 9, 2004; pp. 1462-1463.

Cho, et al; Genome-wide Mapping with Biallelic Markers in Arabidopsis Thaliana; Nature Genetics, vol. 23, Oct. 1999 pp. 203-207.

Di, et al; Dynamic Model Based Algorithms for Screening and Genotyping over 100K SNPs on Oligonucleotide Microarrays; Bioinformatics Advance Access; Jan. 18, 2005.

Hubbell, et al; Fidelity Probes for DNA Arrays; Proc Int Conf Intell Sys Biol. 1999 (abstract).

Liu, et al; Analysis of High Density Expression Microarrays with Signed-Rank Call Algorithms; Bioinformatics; vol. 18; No. 12; 2000; pp. 1593-1599.

Mei, et al; Probe Selection for High-Density Oligonucleotide Arrays; PNAS; Sep. 30, 2003; vol. 100; No. 20; pp. 11237-11242.

Wang: et al; Gene Structure-Based Splice Variant Deconvolution Using a Microarray Platform: Bioinformatics; vol. 19; Suppl. 1; 2003; pp. i315-i1322.

Wang, et al; Large-Scale Identification, Mapping, and Genotyping of Single-Nucleotide Polymorphisms in the Human Genome; Science; vol. 280; May 15, 1998; pp. 1077-1082.

* cited by examiner

Figure 5

Define Each Nucleotide at Each position

Example : GTCA

*Using A as ref. 3 base/position

| i | Position | Base | $S_i$ | |
|---|---|---|---|---|
| 1 | 1 | C | 0 | |
| 2 | 1 | G | 1 | (1st position is G) |
| 3 | 1 | T | 0 | |
| 4 | 2 | C | 0 | |
| 5 | 2 | G | 0 | |
| 6 | 2 | T | 1 | (2nd position is T) |
| 7 | 3 | C | 1 | (3rd position is C) |
| 8 | 3 | G | 0 | |
| 9 | 3 | T | 0 | |
| 10 | 4 | C | 0 | |
| 11 | 4 | G | 0 | (4th position is A as reference) |
| 12 | 4 | T | 0 | |

Concentration Dependence: Slope $$\text{Ln } I = S * \text{Ln } C + \text{Ln } K_{app}$$

$$I = K_{app} * C^S$$

I: Intensity

$K_{app}$: Apparent Affinity Constant

C: Concentration

S: Empirical Value ($0 < S < 1$)

Relationship between Kapp vs. S
- Prediction of Probe Saturation

112 Yeast Clones Randomly Divided into 14 Groups

Groups

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| YNL259C | YNL037C | YAL038W | YHR044C | YMR127C | YLR377C | YOL064C | YPL209C | YIR034C | YJR148W | YEL046C | YGR185C | YBR166C | YOL165C |
| YEL003W | YDR113C | YLR083C | YJL117W | YNL290W | YOL086C | YJR094C | YFL029C | YMR276W | YML060W | YGR072W | YGL181W | YJL155C | YNL227C |
| YDL235C | YGL105W | YLL043W | YMR116C | YMR228W | YJR019C | YIR026C | YGR040W | YMR294W | YDL188C | YMR203W | YGL213C | YEL036C | YNL228W |
| YEL024W | YDR498C | YBR212W | YPL111W | YPR057W | YOR085W | YLR056W | YPR065W | YPL001W | YGR109C | YGR112W | YOL136C | YJL014W | YMR108W |
| YEL018W | YDL029W | YNL015W | YCL055W | YNR035C | YDL226C | YMR270C | YPR191W | YFL039C | YOL043C | YHR208W | YEL037C | YJL110C | YPL043W |
| YER161C | YKL081W | YDL075W | YFR025C | YCL032W | YBL016W | YBR018C | YMR139W | YNL307C | YLR291C | YIL136C | YHL022C | YFL056C | YLR153C |
| YKL193C | YFR053C | YML098W | YLR354C | YIL154C | YBL068W | YBR057C | YPR035W | YGL148W | YDR088C | YOR099W | YHL014C | YJR155W | YPR074C |
| YPR129W | YFL018C | YOL143C | YPL069C | YBR034C | YHR025W | YER118C | YNL005C | YGL155W | YNR015W | YOR176W | YKR061W | YNL231C | YPL089C |

Figure 17

Latin Square Experiment

| Groups \ Exp | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1 | 0 | 0.25 | 0.5 | 1 | 2 | 4 | 8 | 16 | 32 | 64 | 128 | 256 | 512 | 1024 |
| 2 | 0.25 | 0.5 | 1 | 2 | 4 | 8 | 16 | 32 | 64 | 128 | 256 | 512 | 1024 | 0 |
| 3 | 0.5 | 1 | 2 | 4 | 8 | 16 | 32 | 64 | 128 | 256 | 512 | 1024 | 0 | 0.25 |
| 4 | 1 | 2 | 4 | 8 | 16 | 32 | 64 | 128 | 256 | 512 | 1024 | 0 | 0.25 | 0.5 |
| 5 | 2 | 4 | 8 | 16 | 32 | 64 | 128 | 256 | 512 | 1024 | 0 | 0.25 | 0.5 | 1 |
| 6 | 4 | 8 | 16 | 32 | 64 | 128 | 256 | 512 | 1024 | 0 | 0.25 | 0.5 | 1 | 2 |
| 7 | 8 | 16 | 32 | 64 | 128 | 256 | 512 | 1024 | 0 | 0.25 | 0.5 | 1 | 2 | 4 |
| 8 | 16 | 32 | 64 | 128 | 256 | 512 | 1024 | 0 | 0.25 | 0.5 | 1 | 2 | 4 | 8 |
| 9 | 32 | 64 | 128 | 256 | 512 | 1024 | 0 | 0.25 | 0.5 | 1 | 2 | 4 | 8 | 16 |
| 10 | 64 | 128 | 256 | 512 | 1024 | 0 | 0.25 | 0.5 | 1 | 2 | 4 | 8 | 16 | 32 |
| 11 | 128 | 256 | 512 | 1024 | 0 | 0.25 | 0.5 | 1 | 2 | 4 | 8 | 16 | 32 | 64 |
| 12 | 256 | 512 | 1024 | 0 | 0.25 | 0.5 | 1 | 2 | 4 | 8 | 16 | 32 | 64 | 128 |
| 13 | 512 | 1024 | 0 | 0.25 | 0.5 | 1 | 2 | 4 | 8 | 16 | 32 | 64 | 128 | 256 |
| 14 | 1024 | 0 | 0.25 | 0.5 | 1 | 2 | 4 | 8 | 16 | 32 | 64 | 128 | 256 | 512 |

Figure 18

Latin Square Data Sets from Yeast_Test_Hyb Chips

*Lot 1 (9912072)*

| | | | |
|---|---|---|---|
| No Background: | 3 Scans | 14 chips | (530, PMT=701; 570, PMT=701; 570, PMT=600) |
| + Background: | 3 Scans | 14 chips | (530, PMT=701; 570, PMT=701; 570, PMT=600) |

*Lot 2 (9910426)*

| | | | |
|---|---|---|---|
| No Background: | 1 Scan | 14 chips | (570, PMT=600) |
| No Background: | 1 Scan | 14 chips | (570, PMT=600) |

*Lot 3 (9910427)*

| | | | |
|---|---|---|---|
| + Background: | 1 Scan | 14 chips | (570, PMT=526) |
| No Background_Rep1: | 1 Scan | 14 chips | (570, PMT=526) |
| No Background_Rep2: | 1 Scan | 14 chips | (570, PMT=526) |

*Lot 4 (9913514)*

| | | | |
|---|---|---|---|
| No Background: | 1 Scan | 14 chips | (570, PMT=526) |
| + Background: | 1 Scan | 14 chips | (570, PMT=526) |

*Lot 5 (9914059)*

| | | | |
|---|---|---|---|
| + Background_Rep1: | 1 Scan | 14 chips | (570, PMT=526) |
| + Background_Rep2: | 1 Scan | 14 chips | (570, PMT=526) |
| No Background: | 1 Scan | 14 chips | (570, PMT=526) |

Figure 19

YDR113C

Ln(Int) at Different Spike Concentrations

8pM

16pM

32pM

Correlation between Predicted & Observed Ln(Int)'s

Predicted Observed Slopes

CC=0.42

CC=0.84

From Yeast to Human

Using Parameters from Yeast Model System to Predict Human_U95A

METHODS FOR SELECTING NUCLEIC ACID PROBES

RELATED APPLICATIONS

This application claims the priority of U.S. Provisional Application No. 60/252,617, filed on Nov. 21, 2000, which is incorporated herein by reference for all purposes.

This application is related to U.S. patent application Ser. No. 09/721,042, filed on Nov. 21, 2000, entitled "Methods and Computer Software Products for Predicting Nucleic Acid Hybridization Affinity", and U.S. patent application Ser. No. 09/718,295, filed on Nov., 21, 2000, entitled "Methods and Computer Software Products for Selecting Nucleic Acid Probes". Both applications are incorporated herein by reference for all purposes.

BACKGROUND OF THE INVENTION

The present invention relates to methods for designing nucleic acid probe arrays. U.S. Pat. No. 5,424,186 describes a pioneering technique for, among other things, forming and using high density arrays of molecules such as oligonucleotides, RNA or DNA), peptides, polysaccharides, and other materials. This patent is hereby incorporated by reference for all purposes. However, there is still great need for methods, systems and software for designing high density nucleic acid probe arrays.

SUMMARY OF THE INVENTION

In one aspect of the invention, methods and computer software products are provided for selecting nucleic acid probes. In one embodiment, dynamic programming is employed to select a set of k probes from n probes so that the selected probes have a maximum aggregate adjusted quality score.

A computer implemented method for selecting nucleic acid probes is provided. In some embodiments, the methods include steps of inputting quality scores and locations for a plurality (n) of candidate probes; selecting k number of probes from the n number of candidate probes, wherein the selected probes have a maximum aggregate adjusted quality score; wherein the adjusted quality score is based upon the quality score and the overlapping of the selected probes.

In preferred embodiments, the adjusted quality score is calculated according to:

$$S' = S\sqrt{\frac{(l-o)}{l}},$$

where $S'$ is an adjusted quality score; $S$ is a quality score; $l$ is the probe length, $o$ is the overlap the probe has with other probes. The probes are particularly useful for measuring gene expression. In preferred embodiments, the probes are immobilized on a substrate to form nucleic acid probe arrays. In exemplary embodiments, the arrays contain probes for measuring a large number of, at least 50, 100, 500, 1000, 2000, 5000 or 10000 transcripts. Each of the transcripts is detected by a set of probes. The embodiment of the invention is often described for the selection of a set of probes for a single transcript (i.e., k probes from n probes), where k is at least 3, 5, 10, or 15.

While this invention is not limited to any particular optimization methods or algorithm, the preferred embodiments employ dynamic programming optimization to select probes. In some particularly preferred embodiments, the selecting step includes calculating best adjusted quality scores (Score(i,t)) for probe i last with t−1 probes chosen before i and previous location j providing this best score (Last(i,k)); determining the best adjusted quality scores for Score(j, k) to select the last probe; and selecting the next probe according to Last(the probe selected, number of probes remain to be selected); and repeating the selecting step until all k probes are selected.

The exemplary embodiments of the systems for selecting nucleic acid probes include a processor; and a memory coupled with the processor, the memory storing a plurality of machine instructions that cause the processor to perform the methods of the invention.

In some embodiments, the computer software products of the invention include a computer readable medium having computer executable instructions for performing the methods of the invention. Exemplary computer readable medium include CD-ROM, DVD-ROM, Floppy Disk, Hard drive, flash memory or the like.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 5 shows an example of $S_i$ for an exemplary probe.

FIG. 17 shows yeast clones used to produce targets.

FIG. 18 shows a Latin Square design.

FIG. 19 shows Latin Square data sets from yeast_test_hyb chips.

DETAILED DESCRIPTION OF THE PREFERRED EMBODIMENTS

Figure 1:
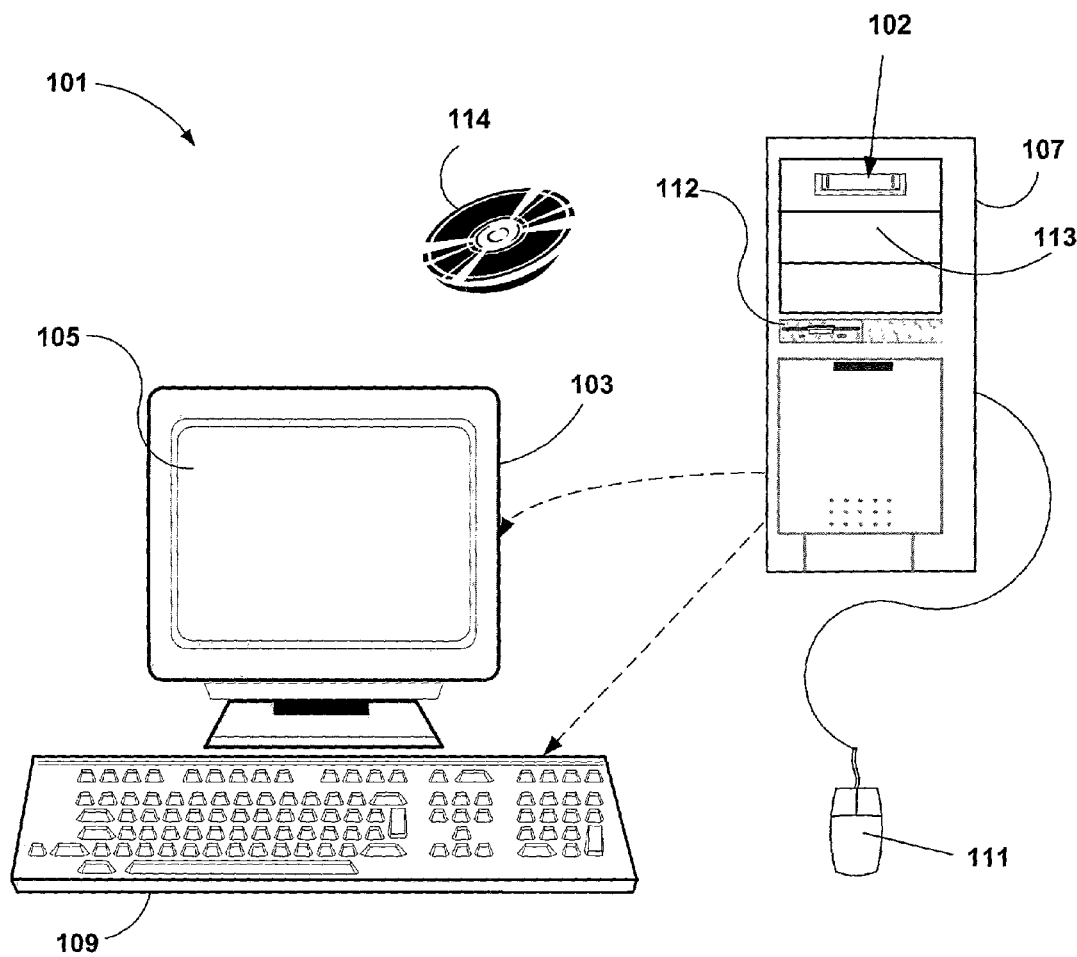
FIG. 1 illustrates an example of a computer system that may be utilized to execute the software of an embodiment of the invention.

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention.

I. Glossary

"Nucleic acids," according to the present invention, may include any polymer or oligomer of nucleosides or nucleotides (polynucleotides or oligonucletodies), which include pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982) and L. Stryer BIOCHEMISTRY, $4^{th}$ Ed., (March 1995), both incorporated by reference. Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. See U.S. Pat. No. 6,156,501 which is incorporated herein by reference in its entirety for all purposes. In addition, the nucleic acids may be DNA or RNA, or a mixture thereof, and may exist permanently or transitionally in single-stranded or double-stranded form, including homoduplex, heteroduplex, and hybrid states. Oligonucleotides and polynucleotides are included in this definition and relate to two or more nucleic acids in a polynucleotide.

"Probe," as used herein, is defined as a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e. A, G. U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages.

"Target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from the context.

An "array" may comprise a solid support with peptide or nucleic acid probes attached to said support. Arrays typically comprise a plurality of different nucleic acids or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767–777 (1991). Each of which is incorporated by reference in its entirety for all purposes. These arrays may generally be produced using mechanical synthesis methods or light directed synthesis methods which incorporate a combination of photolithographic methods and solid phase synthesis methods. Techniques for the synthesis of these arrays using mechanical synthesis methods, such as ink jet, channel block, flow channel, and spotting methods which are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,744,305, 5,770,358, 5,789,162, 5,708,153, 6,040,193 and 5,800,992, which are hereby incorporated in their entirety for all purposes. Arrays may be packaged in such a manner as to allow for diagnostics or other manipulation of in an all inclusive device, see for example, U.S. Pat. Nos. 5,856,174 and 5,922,591, and 5,945,334, which are incorporated herein in their entirety by reference for all purposes. See also U.S. patent application Ser. No. 09/545,207 (pending) which is incorporated herein in its entirety for all purposes for additional information concerning arrays, their manufacture, and their characteristics. It is hereby incorporated by reference in its entirety for all purposes.

II. Probe Selection Systems

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, or CD-ROM, or transmitted over a network, and executed by a processor. For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337.

Computer software products may be written in any of various suitable programming languages, such as C, C++, Fortran and Java (Sun Microsystems). The computer software product may be an independent application with data input and data display modules. Alternatively, the computer software products may be classes that may be instantiated as distributed objects. The computer software products may also be component software such as Java Beans (Sun Microsystems), Enterprise Java Beans (EJB), Microsoft® COM/DCOM, etc.

FIG. 1 illustrates an example of a computer system that may be used to execute the software of an embodiment of the invention. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a CD-ROM or DVD-ROM drive 102, system memory and a hard drive (113)(see also FIG. 2) which may be utilized to store and retrieve software programs incorporating computer code that implements the invention, data for use with the invention and the like. Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
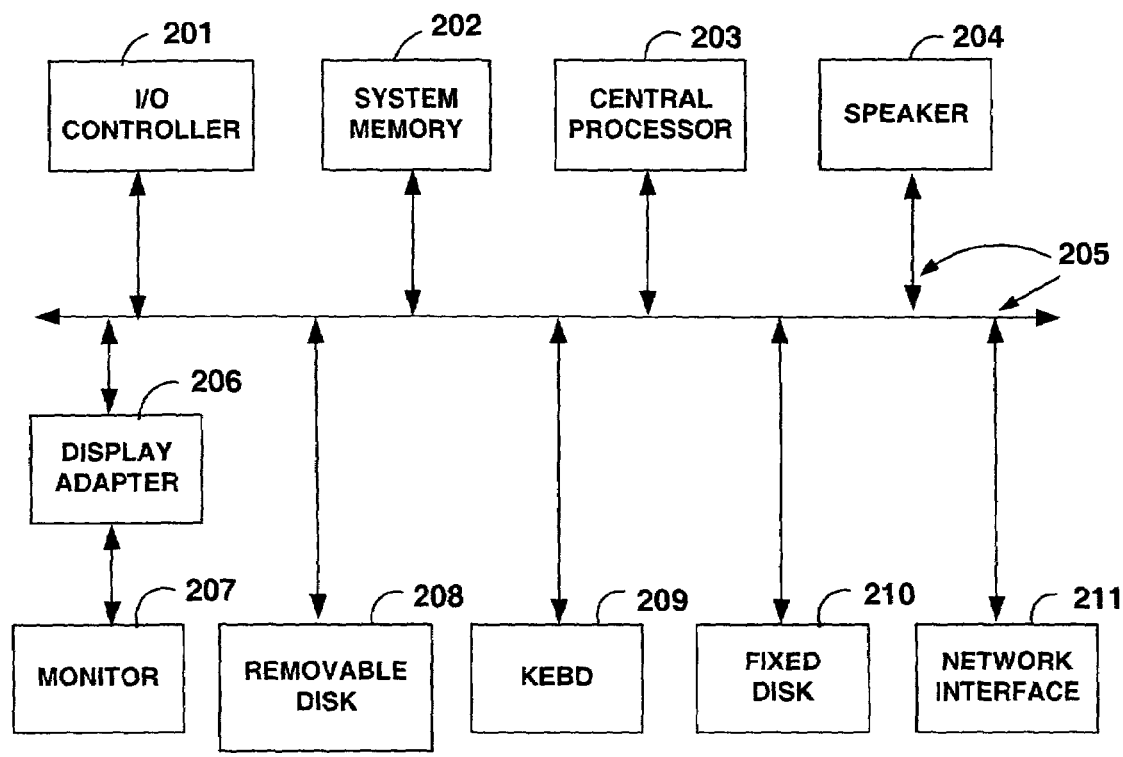
FIG. 2 illustrates a system block diagram of the computer system of FIG. 1.

FIG. 2 shows a system block diagram of computer system 101 used to execute the software of an embodiment of the invention. As in FIG. 1, computer system 101 includes monitor 103, keyboard 109, and mouse 111. Computer system 101 further includes subsystems such as a central processor 203, system memory 202, fixed storage 210 (e.g., hard drive), removable storage 208 (e.g., CD-ROM), display adapter 206, speakers 204, and network interface 211. Other computer systems suitable for use with the invention may include additional or fewer subsystems. For example, another computer system may include more than one processor 51 or a cache memory. Computer systems suitable for use with the invention may also be embedded in a measurement instrument.

III. Methods for Predicting Quality Scores of Probes

In a preferred embodiment, arrays of oligonucleotides or peptides, for example, are formed on the surface by sequentially removing a photoremovable group from a surface, coupling a monomer to the exposed region of the surface, and repeating the process. These techniques have been used to form extremely dense arrays of oligonucleotides, peptides, and other materials. The synthesis technology associated with this invention has come to be known as "VLSIPS™" or "Very Large Scale Immobilized Polymer Synthesis" technology and is further described below.

Additional techniques for forming and using such arrays are described in U.S. Pat. Nos. 5,384,261, and 6,040,193 which are also incorporated by reference for all purposes. Such techniques include systems for mechanically protecting portions of a substrate (or chip), and selectively deprotecting/coupling materials to the substrate. Still further techniques for array synthesis are provided in U.S. Pat. No. 6,121,048, also incorporated herein by reference for all purposes.

Nucleic acid probe arrays have found wide applications in gene expression monitoring, genotyping and mutation detection. For example, massive parallel gene expression monitoring methods using nucleic acid array technology have been developed to monitor the expression of a large number of genes (e.g., U.S. Pat. Nos. 5,871,928, 5,800,992 and 6,040,138; de Saizieu et al., 1998, Bacteria Transcript Imaging by Hybridization of total RNA to Oligonucleotide Arrays, NATURE BIOTECHNOLOGY, 16:45–48; Wodicka et al., 1997, Genome-wide Expression Monitoring in *Saccharomyces cerevisiae*, NATURE BIOTECHNOLOGY 15:1359–1367; Lockhart et al., 1996, Expression Monitoring by Hybridization to High Density Oligonucleotide Arrays. NATURE BIOTECHNOLOGY 14:1675–1680; Lander, 1999, Array of Hope, NATURE-GENETCS, 21(suppl.), at 3, all incorporated herein by reference for all purposes). Hybridization-based methodologies for high throughput mutational analysis using high-density oligonucleotide arrays (DNA chips) have been developed, see Hacia et al., 1996, Detection of heterozygous mutations in BRCA1 using high density oligonucleotide arrays and two-color fluorescence analysis. Nat. Genet. 14:441–447, Hacia et al., New approaches to BRCA1 mutation detection, Breast Disease 10:45–59 and Ramsey 1998, DNA chips: State-of-Art, Nat Biotechnol. 16:40–44, all incorporated herein by reference for all purposes). Oligonucleotide arrays have been used to screen for sequence variations in, for example, the CFTR gene (U.S. Pat. No. 6,027,880, Cronin et al., 1996, Cystic fibrosis mutation detection by hybridization to light-generated DNA probe arrays. Hum. Mut. 7:244–255, both incorporated by reference in their entireties), the human immunodeficiency virus (HIV-1) reverse transcriptase and protease genes (U.S. Pat. No. 5,862,242 and Kozal et al., 1996, Extensive polymorphisms observed in HIV-1 clade B protease gene using high density oligonucleotide arrays. Nature Med. 1:735–759, both incorporated herein by reference for all purposes), the mitochondrial genome (Chee et al., 1996, Accessing genetic information with high density DNA arrays. Science 274: 610–614) and the BRCA1 gene (U.S. Pat. No. 6,013,449, incorporated herein by reference for all purposes).

In one aspect of the invention, a physical model that is based on the thermodynamic properties of the sequence is used to predict the array-based hybridization intensities of the sequence. Hybridization propensities may be described by energetic parameters derived from the probe sequence, and variations in hybridization and chip manufacturing conditions will result in changes in these parameters that can be detected and corrected. Pending U.S. patent application Ser. No. 09/721,042, filed Nov. 21, 2000 and incorporated herein by reference, discloses methods for predicting nucleic acid hybridization affinity.

The values of weight coefficients in the physical model may be determined by empirical data because these values are influenced by assay conditions, which include hybridization and target fragmentation, and probe synthesis conditions, which include choice of substrates, coupling efficiency, etc.

Figure 3:
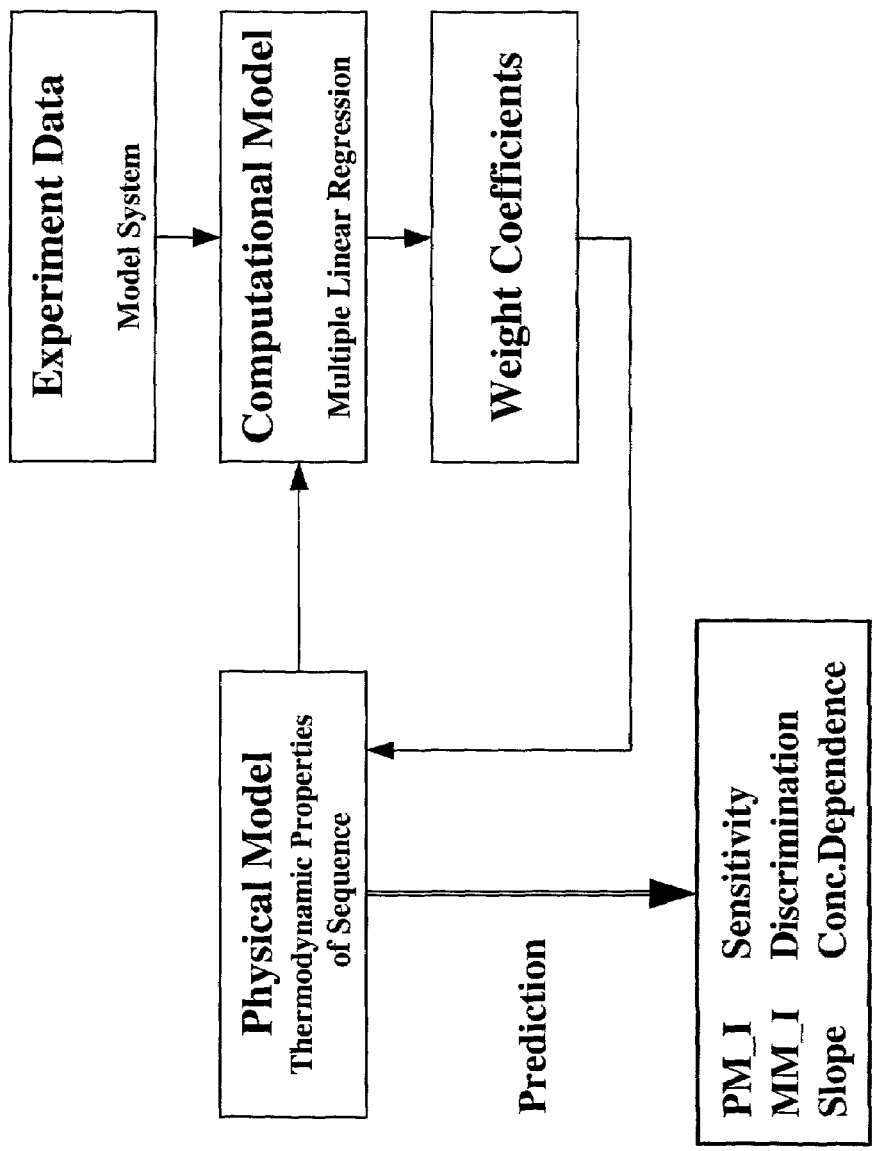
FIG. 3 illustrates a model system for probe sequence-based prediction of probe hybridization behavior (probe quality).

In one embodiment (FIG. 3), a model experimental system is used to generate empirical data and a computational model is used to process these data to solve for the weight coefficients of the physical model. These solved weight coefficients are in turn placed back into the physical model, enabling it to predict the hybridization behaviors of new sequences.

Figure 4:
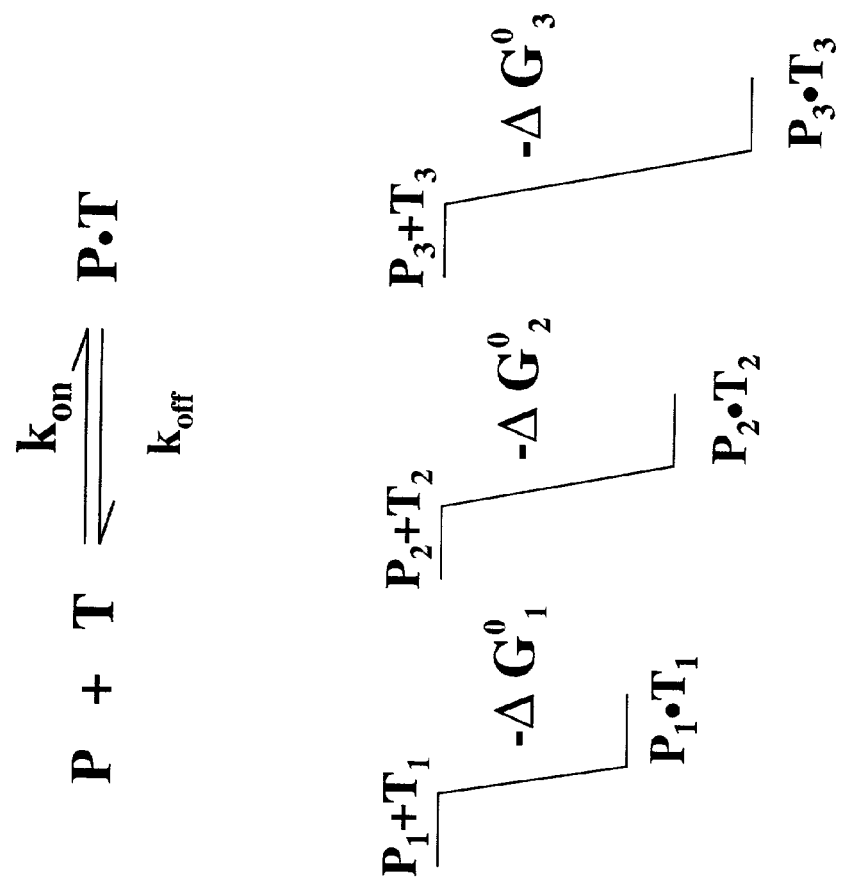
FIG. 4 illustrates a basic physical model for probe target interaction.

The interaction between a probe and its target is described in FIG. 4. Basically, a target (T) hybridizes to its complementary probe (P) to form a probe-target duplex (P·T) (FIG. 4), and the reaction is accompanied with favorable free energy change (FIG. 4). The amplitude of the free energy change (ΔG) determines the stability of probe-target duplex. The duplex stability can be described by equilibrium constant ($K_s$), which is sequence-dependent. The relationship between $K_s$ and ΔG may be given by Boltzmann's equation:

$$K_s = \frac{k_{on}}{k_{off}} = e^{-\Delta G/RT} \quad \text{[Equation 1]}$$

where $k_{on}$ and $k_{off}$ are the rate constants for association and dissociation, respectively, of the probe-target duplex, R is the gas constant and T is the absolute temperature. According to Equation 1, ΔG is a function of the sequence. The dependence of ΔG on probe sequence can be quite complicated, but relatively simple models for ΔG have yielded good results.

There are a number of ways to establish the relationship between the sequence and ΔG. In preferred embodiments, one model (equation 2), shown in pending U.S. application Ser. Number 09/721,042, filed on Nov. 21, 2000, previously incorporated by reference is shown below:

$$\Delta G_{seq} = \sum_{i=1}^{3N} P_i S_i \quad \text{[Equation 2]}$$

or $$\Delta G_{seq} = \sum_{i=1}^{3N} P_i S_i + C \quad \text{[Equation 3]}$$

where N is the length (number of bases) of a probe. $P_i$ is the value of the ith parameter which reflects the ΔG of a base in a given sequence position relative to a reference base in the same position. In preferred embodiments, the reference base is A. In this case, the Pi's will be the free energy of a base in a given position relative to base A in the same position. FIG. 5 shows an example of how the value of $S_i$ is determined based upon the sequence of a probe. In this example, a probe, GTCA has N=4 and thus, it has 3×4=12 $S_i$ values. Each probe base position has three S values, each for a different possible base. In this example, possible bases are evaluated in the sequence of C, G, and T (A is the reference base). However, one of skill in the art would appreciate that the assignment of this particular base sequence is arbitrary. Alternative evaluation sequence, such as G, C, and T may also be used as long as the same scheme is used for model building and for hybridization affinity prediction.

Based on the simple hybridization scheme described in FIG. 4, the hybridization intensity is proportional to the concentration of probe-target duplex, where $C_0$ is constant (Equation 4). Under equilibrium condition, the intensity is directly related to ΔG (Equation 5). This relationship is also expressed in natural logarithm form, where $C_1$ and $C_2$ are constants (Equation 7) and Equation 6 also holds for approaching equilibrium cases. According to Equation 2, the relationship between intensity and probe sequence is described in Equation 7 and 8:

$$I = C_0[P \cdot T] \quad \text{[Equation 4]}$$

$$[P \cdot T] = K_s[P][T] = e^{-\Delta G/RT}[P][T] \quad \text{[Equation 5]}$$

$$\text{Ln } I = -\Delta G/RT + \text{Ln}\{C_0[P][T]\} \quad \text{[Equation 6]}$$

$$LnI = C_1 \sum_{i=1}^{3N} P_i S_i + C_2, \text{ where } C_2 = \text{Ln}\{C_0[P][T]\} \text{ and } C_1 = -1/RT \quad \text{[Equation 7]}$$

or $$LnI = \sum_{i=1}^{3N} C_1 P_i S_i + C_2 = \sum_{i=1}^{3N} W_i S_i + C_2 \quad \text{[Equation 8]}$$

where $W_i = C_1 P_i$. The following is a linear regression model for probes of N bases in length using a training data set that contains intensity values of M probes.

$$\text{Ln}(I_1) = W_1 S_{11} + W_2 S_{21} + \ldots W_{3N} S_{3N1}$$

$$\text{Ln}(I_2) = W_1 S_{12} + W_2 S_{22} + \ldots W_{3N} S_{3N2}$$

$$\text{Ln}(I_1) = W_1 S_{11} + W_2 S_{12} + \ldots W_{3N} S_{3N1}$$

Hybridization intensities (relative to a reference base, such as an A) for each type of bases can be solved at each position in the probe sequence may be predicted. Multiple linear regression analysis is well known in the art, see, for example, the electronic statistics book Statsoft, available on the World Wide Web; Darlington, R. B. (1990). *Regression and linear models.* New York: McGraw-Hill, both incorporated by reference for all purposes. Computer software packages, such as SAS, SPSS, and MatLib 5.3 provide multiple linear regression functions. In addition, computer software code examples suitable for performing multiple linear regression analysis are provided in, for example, the Numerical Recipes (NR) books developed by Numerical Recipes Software and published by Cambridge University Press (CUP, with U.K. and U.S. web sites).

Figure 6:
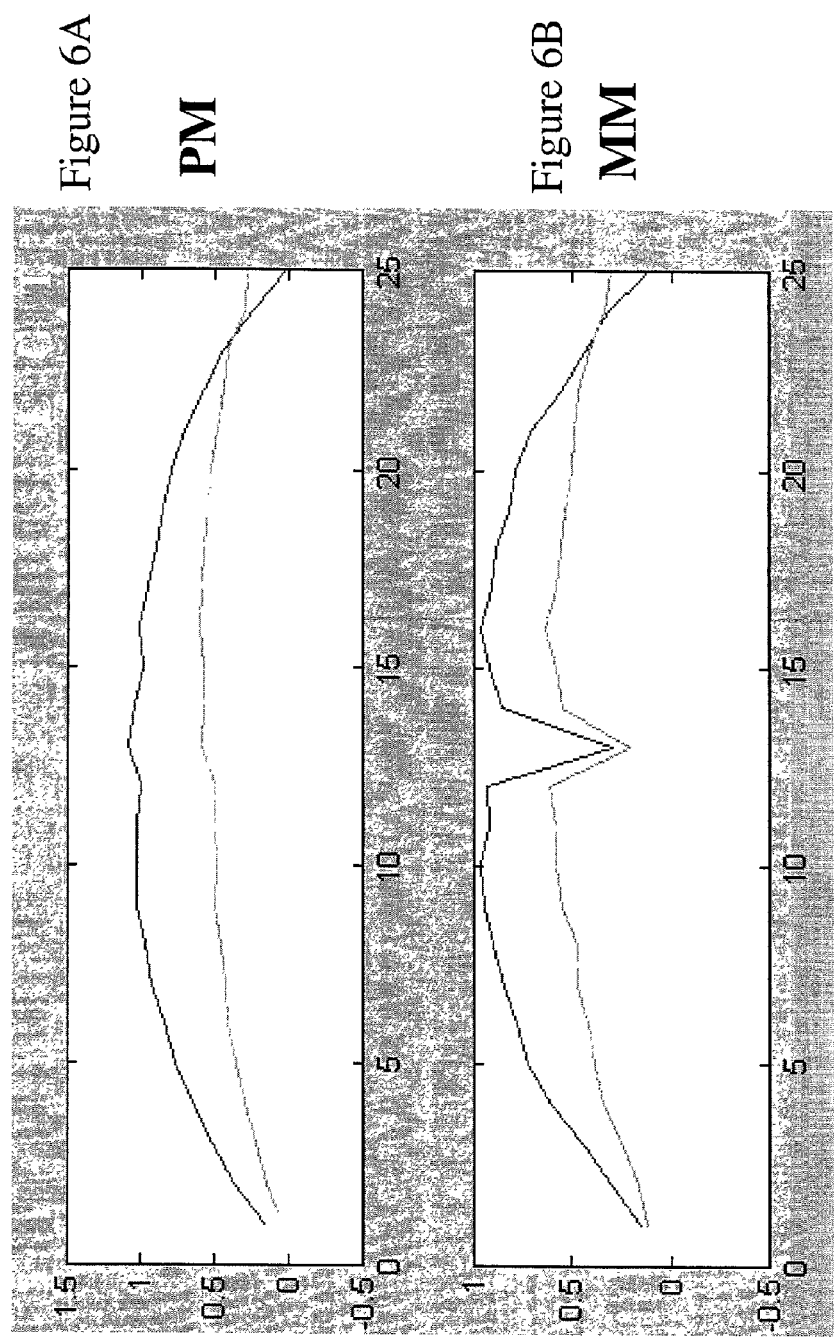
FIGS. 6A and 6B show predicted relative $\Delta G$ for perfect match and mismatch probes.

In a preferred embodiment, a set of probes of different sequences (probes 1 to M) is used as probes in experiments(s). Hybridization affinities (relative ΔG or Ln (I)) of the probes with their target are experimentally measured to obtain a training data set (see, example section infra). Multiple linear regression may be performed using hybridization affinities as $I[I_1 \ldots I_m]$ to obtain a set of weight coefficients: $[W_1 \ldots W_N]$. The weight coefficients are then used to predict the hybridization affinities using Equation 7. FIG. 6A shows relative predicted ΔG at every base position in a probe of 25 bases in exemplary experiments (see the example section infra for a detailed description of experimental conditions).

In addition, in some embodiments, by using intensities derived from mismatch probes that are probes designed to contain one or more mismatch bases from a reference probe, a set of weight coefficients may be obtained to predict the mismatch intensity using perfect match probe sequence. FIG. 6B shows an example for predicting mismatch hybridization affinity at center base position.

Figure 7:
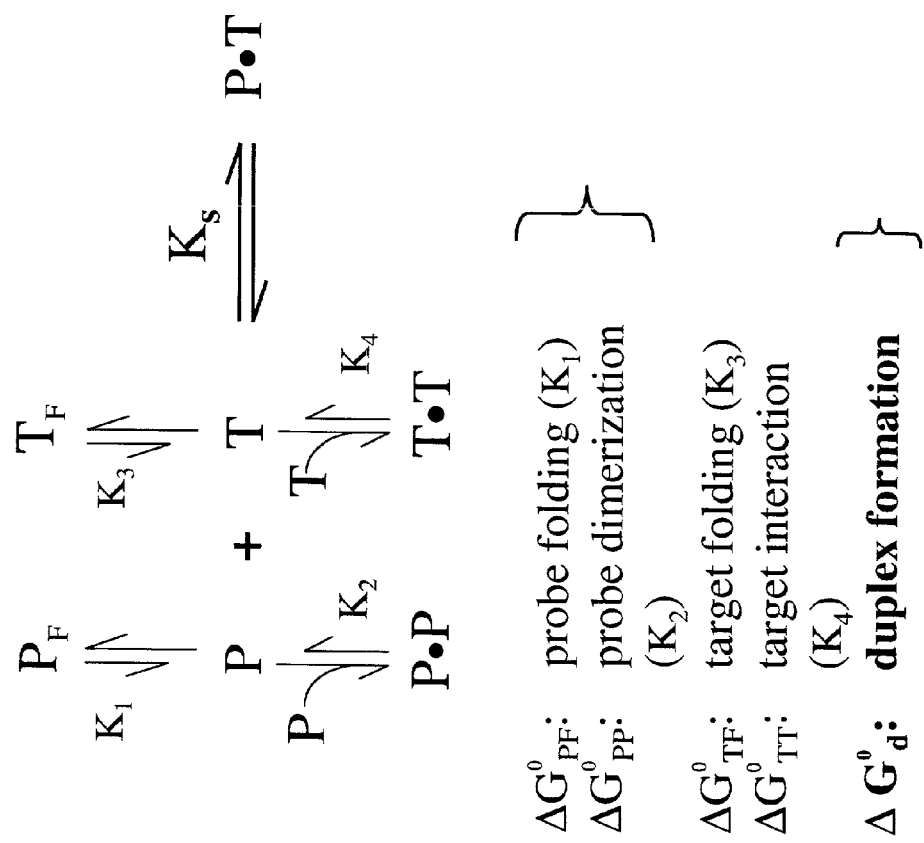
FIG. 7 shows an overall reaction of probe target formation.

Since other interactions such as probe self-folding, probe-to-probe interaction, target self-folding and target-to-target interaction also interfere with the probe-target duplex formation, their contributions to the values of the weight coefficients may also be considered. FIG. 7 shows an overall equilibrium scheme including the formation of a probe-target duplex (PT), probe self-folding ($P_F$) and probe dimerization (PP). Probe folding renders the probe unavailable for binding with the target. Probe dimerization renders two probes unavailable for binding with the target. In some embodiments, the hybridization affinity prediction model accounts for probe folding and probe dimerization:

$$\Delta G_{overall}^0 = -W_d \Delta G_d^0 + W_{PF} \Delta G_{PF}^0 + W_{PP} \Delta G_{pp}^0 \quad \text{[Equation 9]}$$

$$\ln I = C_1 \Delta G_{overall}^0 + C_2 \quad \text{[Equation 10]}$$

where $W_d$ is the weight for sequence based probe affinity; $W_{PF}$ is the weight for probe formation and $W_{pp}$ is the weight for probe dimerization. Any methods that are capable of predicting probe folding and/or probe dimerization are suitable for at least some embodiments of the invention for predicting the hybridization intensity in at least some embodiments of the invention. In a particularly preferred embodiment, Oligowalk (available on the World Wide Web may be used to predict probe folding.

One important criterion of probe selection for a quantitative gene expression assay is that hybridization intensities of the selected probes must correspond to target concentration changes. In some embodiments, the relationship between concentrations and intensities of a probe is modeled as:

$$\text{Ln}(I) S \text{Ln} C + \text{Ln} K_{app} \quad \text{[Equation 11]}$$

or $$I = K_{app} C^S \quad \text{[Equation 12]}$$

where I is intensity; $K_{app}$ is apparent affinity constant; C is concentration of the target; and S is an empirical value corresponding to the slope of the line relates Ln I and Ln C ($0 < S < 1$) (see FIG. 8).

Figure 8:
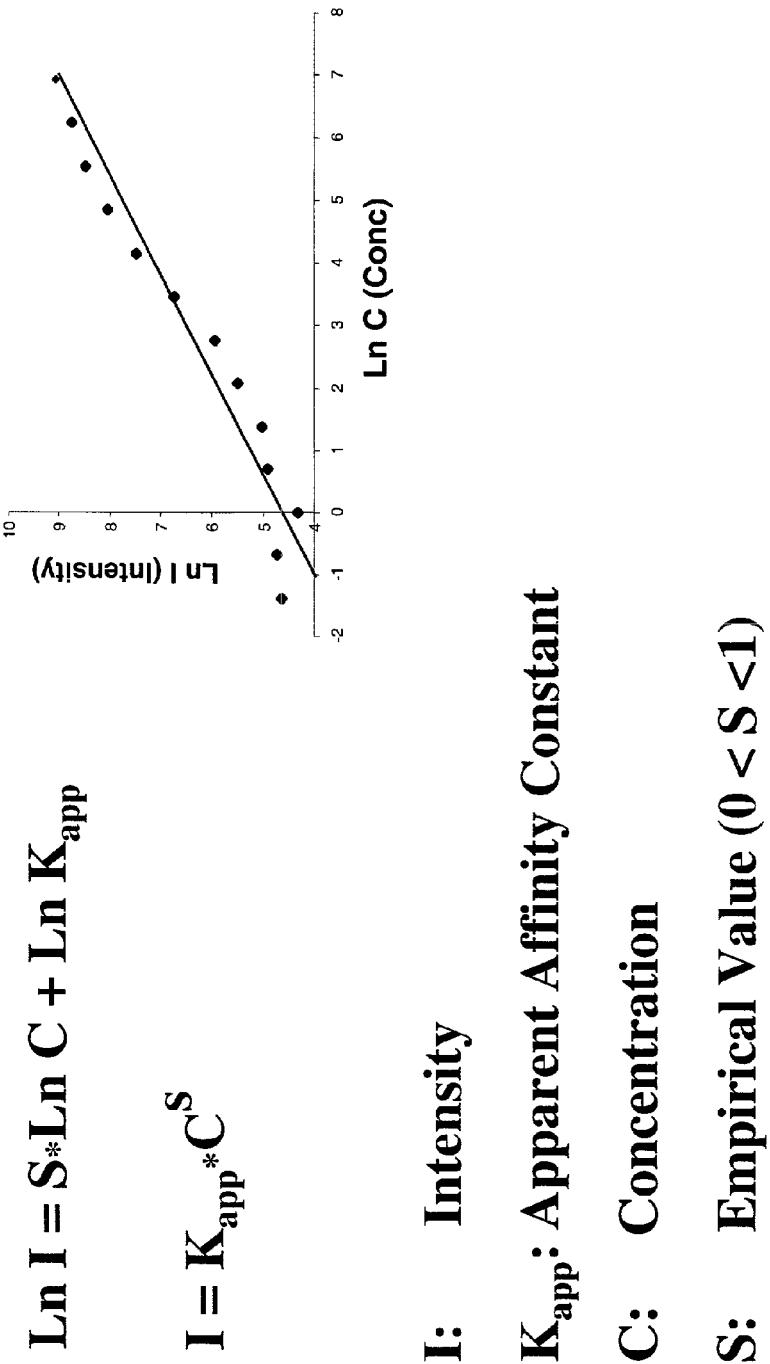
FIG. 8 shows concentration dependency of hybridization intensity.
Figure 9A:
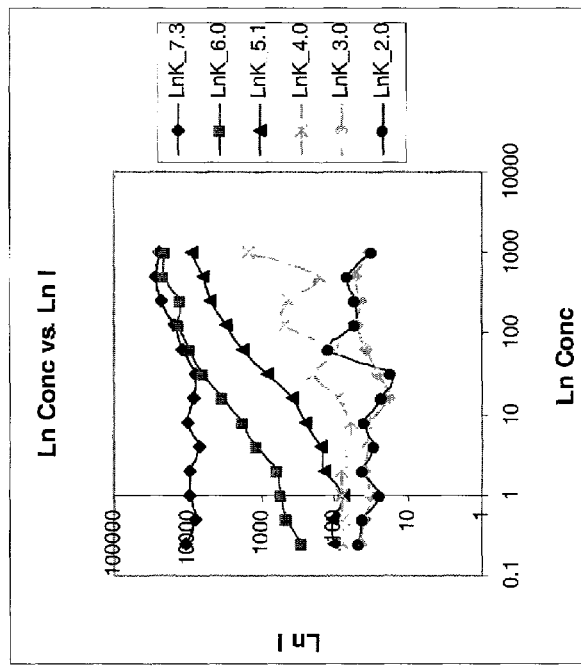
FIGS. 9A and 9B show the relationship between probe-target binding affinity ($K_{app}$) and the slope (S).
Figure 9B:
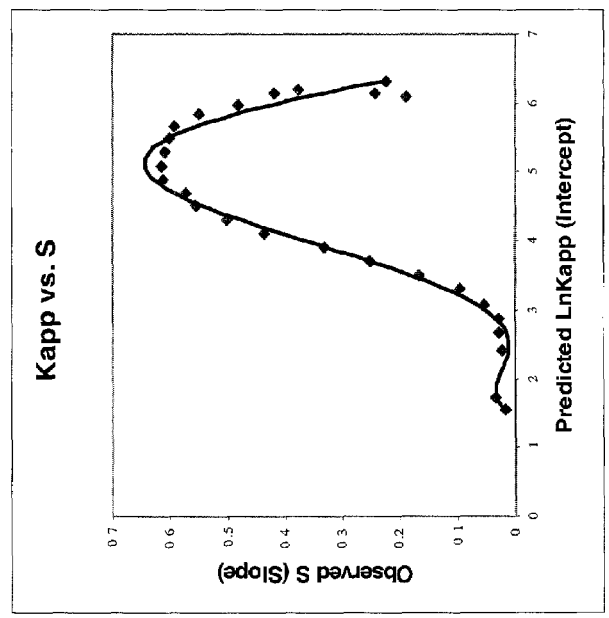
Figure 26:
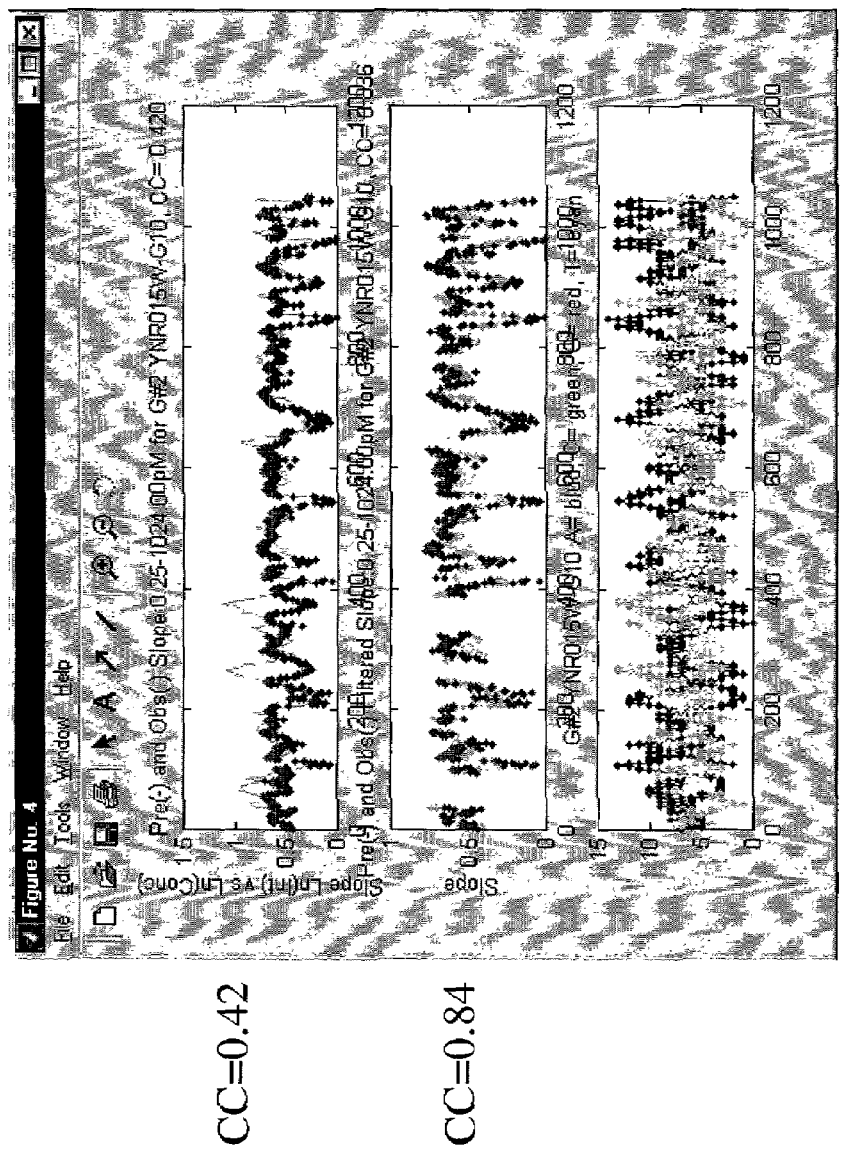
FIG. 26 shows predicted versus observed slopes and improvement of correlation between the two slopes after filtering saturated probes.

Equation 12 describes the relationship between hybridization intensities of probes and target concentration. For example, when S is equal to 1, the intensities of a probe linearly correspond to its target concentration (FIG. 8). Thus, based on the S values of the probe, one can select probes that have good concentration dependence. FIG. 9A shows the polynomial relationship between S and Ln $K_{app}$, indicating that when the value of Ln $K_{app}$ increases to a certain level the value of S reaches a plateau before starting to decrease. This relationship allows the identification of not only low hybridization affinity probes (FIG. 9B, bottom lines) but also GC-rich probes that have high affinity but bind to both specific and non-specific targets (FIG. 9B, top line). These GC-rich probes have high intensities, but the intensities maintain constant when target concentration changes (FIG. 9B, top line). Therefore, these probes have small slopes. In some embodiments, linear regression modeling alone will not identify probes with a high propensity to saturate. That is because the linear model for each target concentration will predict the intensity that a probe would have had if it could bind to an unlimited amount of target. Therefore, the predicted slope can be quite high when the observed slope is low (FIG. 26, top). The well-behaved relationship between predicted Ln $K_{app}$ and observed slope allows filtering probes with a high propensity to saturate based on the predicted Ln $K_{app}$ for the given probe. If Ln $K_{app}$ is above a cutoff value (e.g., 5, 6, 7, 8, 9, or 10, FIG. 9), then the probe is effectively filtered as a candidate for probe selection. FIG. 26 (middle) shows the predicted slope profiles after filtering as well as the significant improvement in the overall correlation after these regions are removed.

IV. Methods and Software for Selecting Probes

Figure 10:
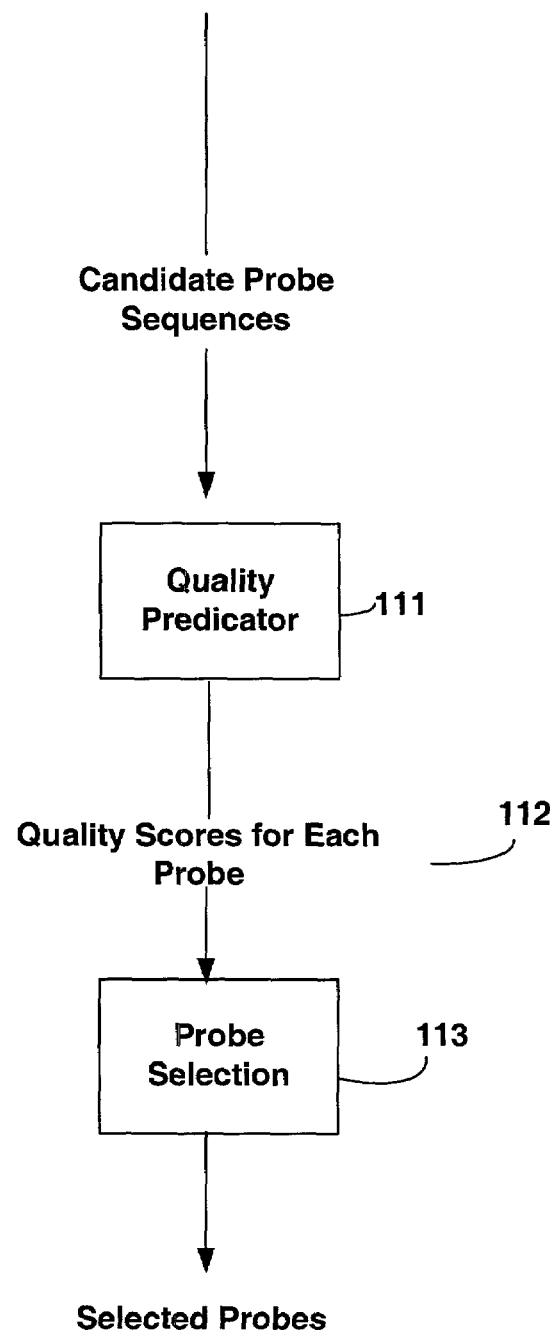
FIG. 10 shows an embodiment of a process for selecting probes.
Figure 11:
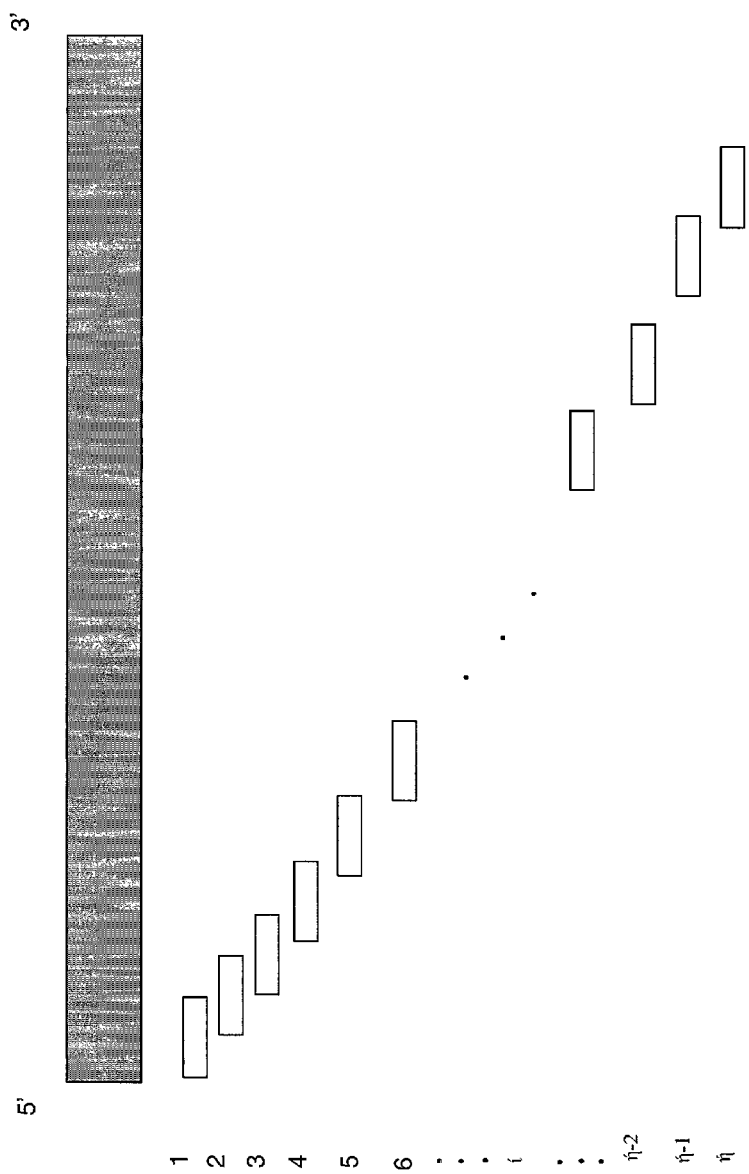
FIG. 11 shows a pool of candidate probes.

FIG. 10 shows a computer-implemented process for selecting probe sequences from a pool of candidate probes. In this particular embodiment, the sequences of a pool of candidate oligonucleotide probe are processed by a quality predictor (101). Throughout this application, the term probe may refer to the sequence of a probe. The pool of candidate oligonucleotide probes may be all possible probes against a particular target or targets. Typically, oligonucleotide probes are at least 10, 15, 20, 25 and 30 bases in length. Polynucleotide probes can be more than 10, 20, 25, 30, 100, 200, 500, 1000, or 5000 bases in length. FIG. 11 illustrates a complete pool of candidate oligonucleotide probes (unfiled rectangle boxes) against a target (black rectangle box). Each of the probes is designed to be complementary to the target sequence. In this particular embodiment, the oligonucleotides are 25 mers. The first probe is complementary to bases 1–25 (from the 5' end) of the target sequence. The second probe is complementary to bases 2–26 and so on. While a complete pool is often desirable, it is not necessary to have a complete pool for at least some embodiments of the invention. In some cases, filters may be used to remove some of the probes from the pool.

The input to the quality predictor (FIG. 10, 101) is the sequence of a pool of candidate probes. One of skill in the art would appreciate that the format of input is not critical. In some embodiments, the probe sequences may be inputted from one or a number of probe sequence files. The file(s) may be plain text file(s), in the FASTA format or other suitable file format. Alternatively, the input may be a stream from other sources such as a data pocket stream from a remote networked computer.

The quality predicator is a software module that calculates quality scores (the term score refers to any qualitative and quantitative values with regard to desired properties of a probe) for probes based upon the sequences of probes. In some embodiments, the quality score may include predicted values such as perfect match intensity, mismatch intensity and/or slope.

Probe selection module (103) selects probes based upon their scores. In preferred embodiments, the quality scores are combined to obtain a unified score. In some cases, the unified quality score is the simple summation of quality scores (e.g., Unified Quality Score=Perfect Match Intensity+Mismatch Intensity+Slope). The selection of probes may be based upon the scores only. For example, if a certain number of probes are desired, the probes with the highest scores are selected until enough number of probes are selected. Alternatively, a threshold-unified score may be established. Probes that have scores higher than the threshold score are selected.

In a preferred embodiment, the goal of the probe selection step is to find the best probes to represent a sequence. The probe selection software module takes a set of probes and a set of quality measures for each probe. It then implements an optimization algorithm to find the best n probes, spread out across the gene. Methods for probe selection using optimization algorithm is described in abandoned U.S. Provisional Application No. 60/252,617, filed Nov. 21, 2000, and incorporated herein by reference in its entirety for all purposes.

Figure 12:
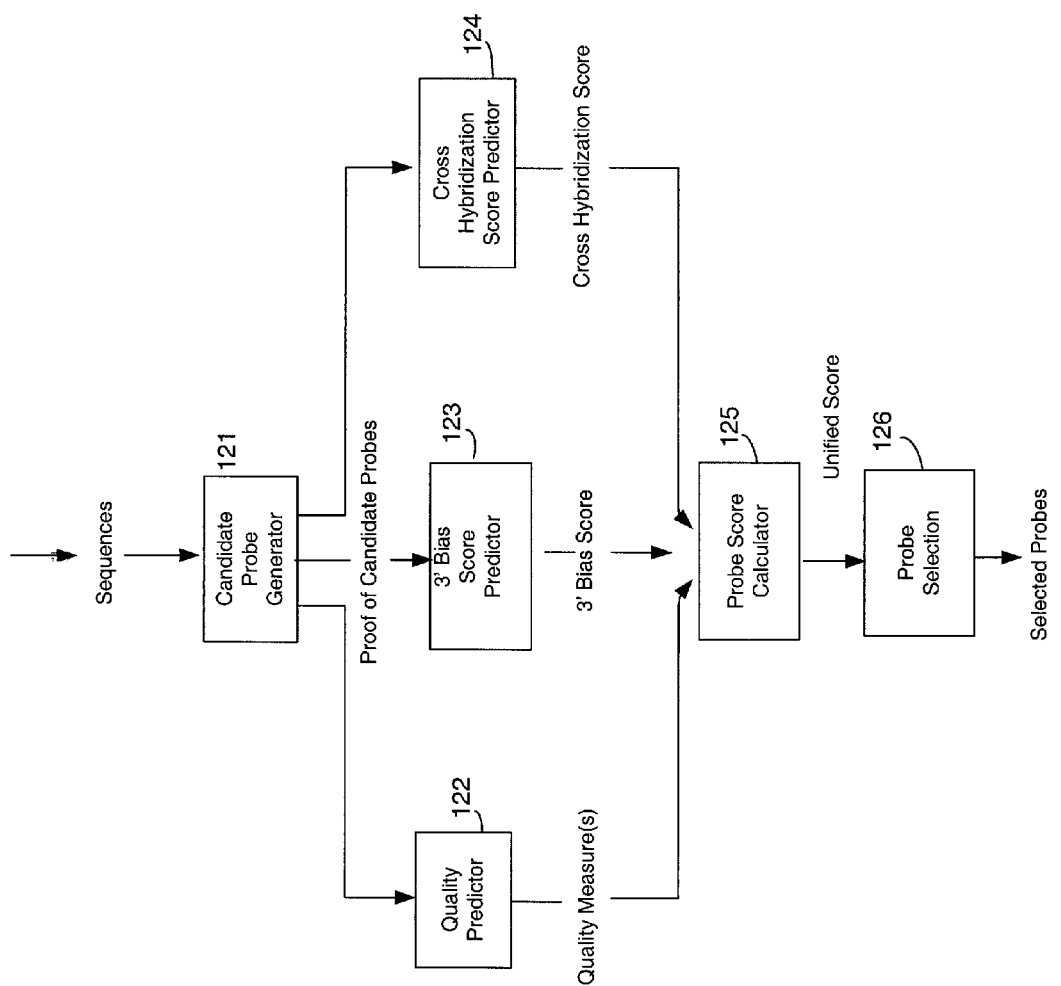
FIG. 12 shows another embodiment of a process for selecting probes.

FIG. 12 shows another embodiment of the computer implemented probe selection process of the invention. Target sequences are inputted to a candidate probe generator (121) which produce either all possible probes of certain length or a subset of the all possible probes. The candidate probe sequences are fed to the quality score predictor (122) for calculating quality measures (scores, e.g., perfect match intensity, mismatch intensity and/or slope). The candidate probe sequences are also fed to a 3' bias score predictor (123) to obtain 3' bias scores that indicates the distance of probe sequence from the 3' end of target sequence. Since the current target preparation method is 3' biased, it is important to select probes that fall into range where its target will be made. The probe sequences may optionally be inputted into a cross hybridization score predictor (124) to calculate cross hybridization scores. The quality scores, 3' bias scores and/or cross hybridization score are combined by a probe score calculator module (125) to produce a unified score. A probe selection module (126) picks the probes with the desirable score.

Figure 13:
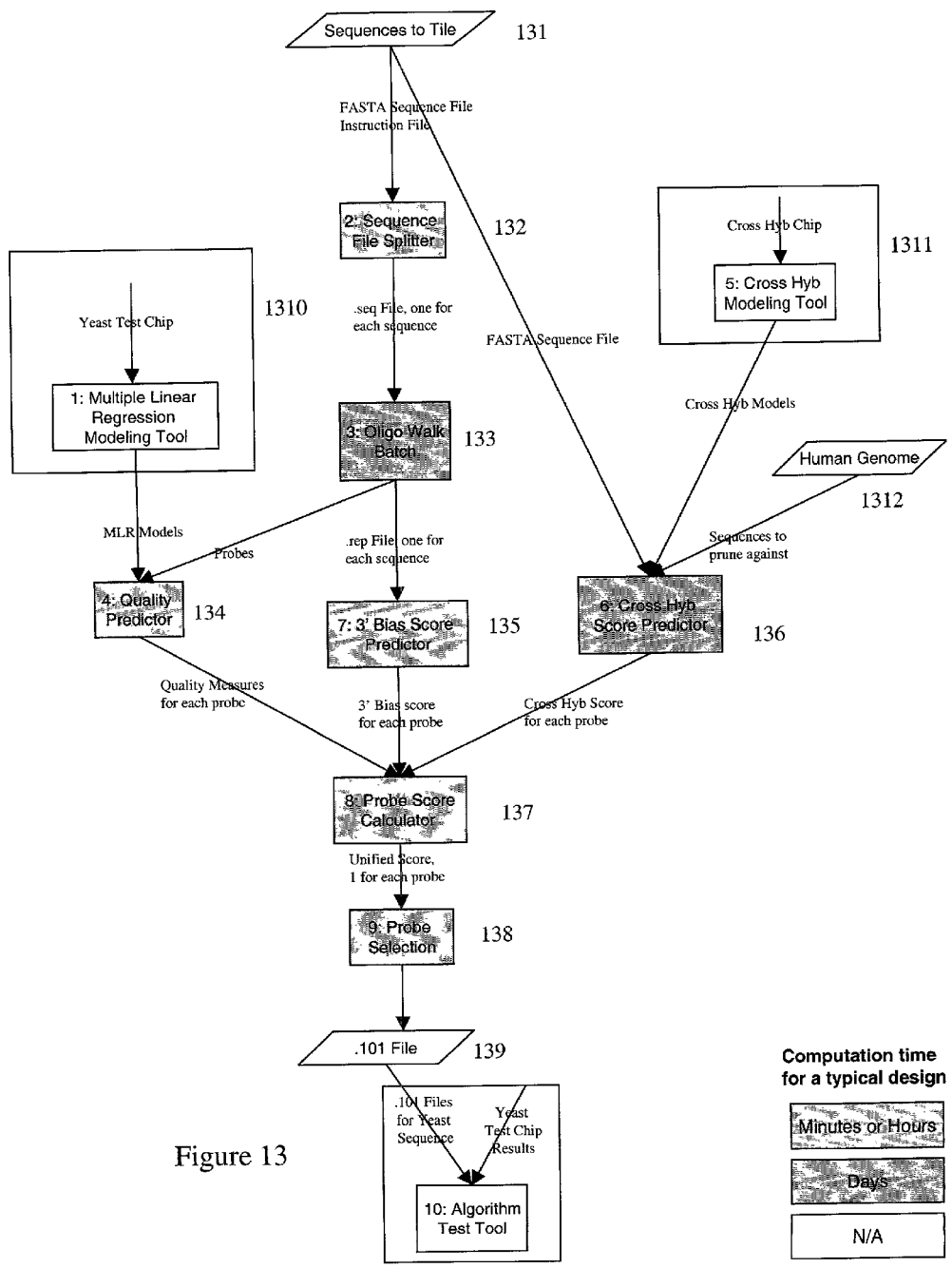
FIG. 13 shows yet another embodiment of a process for selecting probes.

FIG. 13 shows a complete computer implemented probe selection process. In this preferred embodiment, target sequences (131) are used to generate a pool of candidate probes. The probe sequences are stored in a FASTA sequence file. A sequence file splitter (132) divides probe sequences to .seq file which store one sequence per file. The .seq files are processed using an OligoWalker batch tool (133) to produce a .rep file, one for each probe sequence. The .rep files contain ΔG values for the probes. The rep files are inputted into a quality predictor (134). The quality predictor is based upon multiple linear regression models derived from experiment data using, for example, yeast test chips (see also, example section below) (1310). The quality predictor calculates quality scores (measures, perfect match intensity, mismatch intensity and slope) as described above in section II. The rep file is also inputted into a 3' bias score predictor (135) to estimate 3' bias scores for the probes.

The multiple probe FASTA sequence file is also inputted into a cross hybridization predictor (136) to predict a cross hybridization score. The cross hybridization score predictor is based upon models (such as multiple linear regression models) derived from experiment data (1311). In some embodiments, cross hybridization may also be evaluated by pruning probe sequences against a human genome data base (1312) which may be residing locally, in a local area network or in a remote site such as the Genbank.

The quality measures, 3' bias scores and cross hybridization scores are combined by the probe score calculator (137) to produce a unified score for each probe. The combined score is then used for selecting probes (138). The probe selection module takes a set of probes and a set of quality measures for each probe. It then implements a dynamic programming algorithm to find the best n probes, spread out across the gene. The selected probe sequences are stored in .101 files (139).

The following tables describe the various software modules in the exemplary embodiments described in FIG. 13.

| 1: Multiple linear regression modeling tool | |
|---|---|
| Description | Calculates the weights for the regression model. Its is a one time calculation. The results of the calculations will be used every time a new chip is designed. |
| Input | Yeast Test Chip, available from Affymetrix, Santa Clara, CA |
| Output | Multiple linear regression models, a set of weights. |
| Part of chip design | In this embodiment, it is not part of the software package for chip design. It is used as a one-time external process. However, in other exemplary embodiments, it may also become part of the software. |

| 2: Sequence file splitter | |
|---|---|
| Description | Splits a FASTA file of sequences into several sequence files one for each sequence in the instruction file. If max files in folder is greater than 0, subfolders are created in the output path. Each subfolder gets up to the maximum files specified. |
| Input | FASTA file<br>Instructions file<br>Output path<br>Max files in one folder |
| Language/Tool | Java |

| 3: Oligo Walk batch tool | |
|---|---|
| Description | Runs Oligo Walk in batch mode. Oligo Walk produces a .rep file for each sequence. The .rep file contains a delta G value for each probe |
| Input | Batch of .seq files |
| Output | .rep file. The .rep file identifies a probe by a number and a sequence. The sequence is a reverse complement of the 25-mer it represents on the input sequence. The number is the beginning of the probe. |
| Part of chip design | Yes |
| Language/Tool | Microsoft ® Visual Basic |

| 4: Quality predictor | |
|---|---|
| Description | Takes in the MLR model measures and delta G values from Oligo Walk and produces 3 quality measures, perfect match intensity, mismatch intensity and slope. |
| Input | .rep file produced from Oligo Walk |
| Output | 3 Quality measures for each probe. The probe is described as in the input format. |
| Part of chip design | Yes |
| Language/Tool | C |

| 5: Cross Hyb Modeling Tool | |
|---|---|
| Description | Analyzes the results of the yeast cross hyb chip to create a model for predicting the cross hyb score for a probe, based on the number of mismatches and positions of mismatches with 1 or more matching sequences. |
| Input | Results from the cross hyb chip |
| Output | A model that relates number of mismatches and positions of mismatches to a cross hyb score. |
| Part of chip design | In some embodiments, it is not part of the chip design package. Alternatively, it can be part of the package. |

| 6: Cross Hyb Score Predictor | |
|---|---|
| Description | Predicts a cross hyb score for a given set of probes. Its does so by matching the given probes with a genome and assigns a numeric score using the cross hyb models. |
| Input | Cross hyb models<br>A genome<br>Set of probes |
| Output | List of probes and corresponding cross hyb scores |
| Part of chip design | Yes |

| | 7: 3' Bias Score Predictor |
|---|---|
| Description | Predicts the 3' bias score for a given set of probes. Earlier it was believed that most sequences have a sigmoid graph for the 3' bias. But, recently used sequences do not always follow the pattern Therefore, it is important to first study the 3' bias effect and then design a measurement model. |
| Input | Set of probes |
| Output | List of probes and corresponding 3' bias scores |
| Part of chip design | Yes |

| | 8: Probe Score Calculator |
|---|---|
| Description | Given a set files with probe information and scores, this program matches each probe in each sequence and calculates 1 unified score for each probe. |
| Input | Set of probes<br>Set of measures for each probe, each in a different file(s)<br>3 quality scores (probes defined in OligoWalk format)<br>cross hyb score (probes defined in chip design format)<br>3' bias score (probes defined in chip design format) |
| Output | List of probes with a corresponding score. |
| Part of chip design | Yes |

| | 9: Probe selection algorithm |
|---|---|
| Description | Finds the best probes to represent a sequence. It takes a set of probes and a set of quality measures for each probe. It then implements a dynamic programming algorithm to find the best n probes, spread out across the gene. |
| Input | Set of probes<br>Set of measures for each probe<br>3 quality scores<br>cross hyb score<br>3' bias score<br>Number of probes to choose |
| Output | .1lq file |
| Part of chip design | Yes |
| Language/Tool | C |

| | 10: Algorithm Test Tool |
|---|---|
| Description | Tests the new probe selection algorithm. The probe selection algorithm is used to select probes for the known, Yeast test chip. The selected probes are analyzed for their intensity, slope and discrimination values on the yeast test chip. |
| Input | Probes selected for the sequences on the yeast test chip<br>Results from the yeast test chip |

V. Dynamic Programming for Probe Selection

When DNA arrays are constructed, it is vitally important to choose the best set of probes for the type of analysis that will be done. In particular, for any particular application, it is possible to assign scores to the probes (such as the quality score described above), so that probes with higher scores are more likely to be better suited for a particular application than others. Given a set of probes with scores, it is desirable to pick the best set of probes.

In selecting multiple nucleic acid probes for one target, one complication that arises is that probes that are nearby each other are mostly redundant. The amount of new data observed from a probe that overlaps with another probe by 24 bases out of 25 is minimal, so that even if such a probe has a high quality score, it may be desirable to pick another probe that has a lower quality score, but has no or less overlaps with other probes.

In one aspect of the invention, methods are provided to adjust the quality score for each probe corresponding to the amount of information it would provide. In some embodiments of the methods, the following rules are used to adjust the score:

1) Probes that do not overlap have full scores;

2) Probes that do overlap have a penalty that decreases as the amount of penalty decreases;

3) Scores are correlated with information provided;

4) Adding scores provides a reasonable estimate of "total information"

5) It is only necessary to consider overlap with the previous probe for estimating new information.

Figure 14:
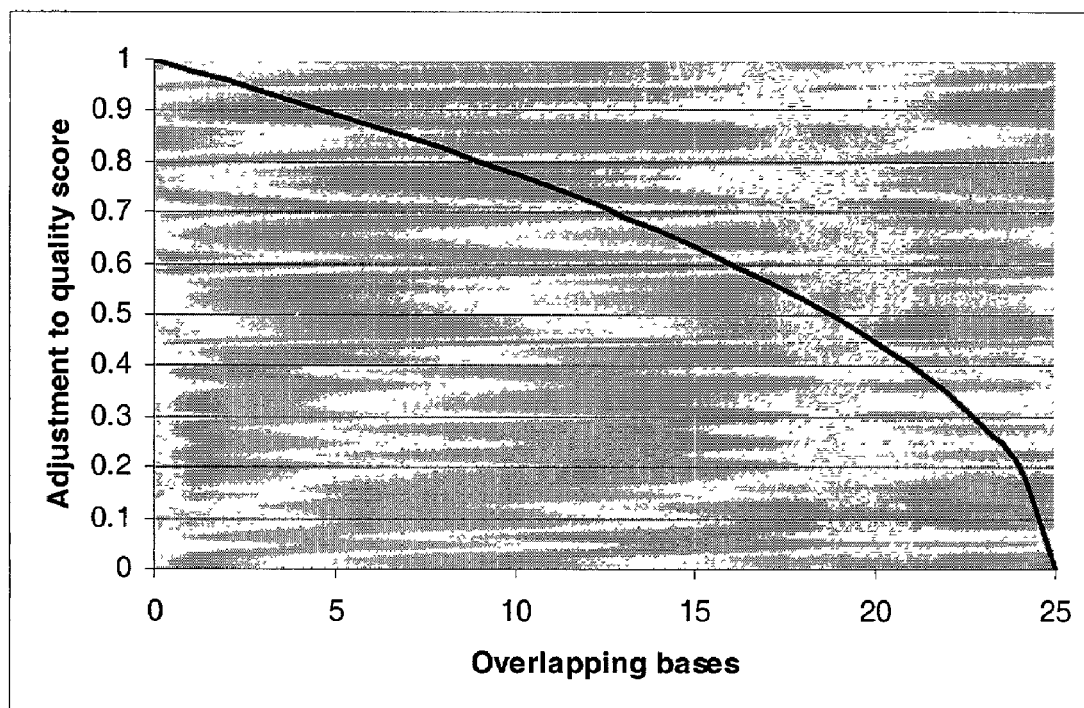
FIG. 14 shows relationship between overlap of a probe with other probes and the adjustment to quality score in one embodiment of the method of the invention.

In particularly preferred embodiments, the quality score is adjusted as follows:

$$S' = S\sqrt{\frac{(l-o)}{l}},$$

where S' is adjusted score; S is initial score; l is the probe length, o is the overlap the probe has with other probes. FIG. 14 shows the relationship between overlapping bases and the penalty that may be applied when the probes are of 25 bases in length. In the preferred embodiments, if a probe has no overlap over other probe(s), the adjustment is 1.0 or no penalty. The penalty increases as the number of overlapping bases increases. For example, if a probe has 10 overlapping bases, the adjustment quality score is about 77% of the original quality score. For a probe with 24 bases overlapping with other probes, the original quality score is adjusted for a 80% penalty because of the additional information content provided by this probe in view of the other probes is small.

One of skill in the art would appreciate that the methods of the invention are not limited to any particular methods for adjusting quality scores.

In one aspect of the invention, optimization methods are used to pick an optimal set of k probes from n probes provided with initial scores and locations of the probes in the target sequence. The optimal set of k probes is chosen for its high (optimal) aggregate, not individual adjusted score. In a typical gene expression experiment, k may be at least 3, 5, 10, 15, 20, 25, 30, 40 or 50 for a single transcript. The selection process may be described with reference to a single transcript and the selection of a single set. The methods are particularly useful for selecting probes against a large number of transcripts, for example, at least 100, 200, 300, 500, 1000, 2000, 5000, or 10000. A set of probes may be selected for each of the transcripts.

Figure 15:
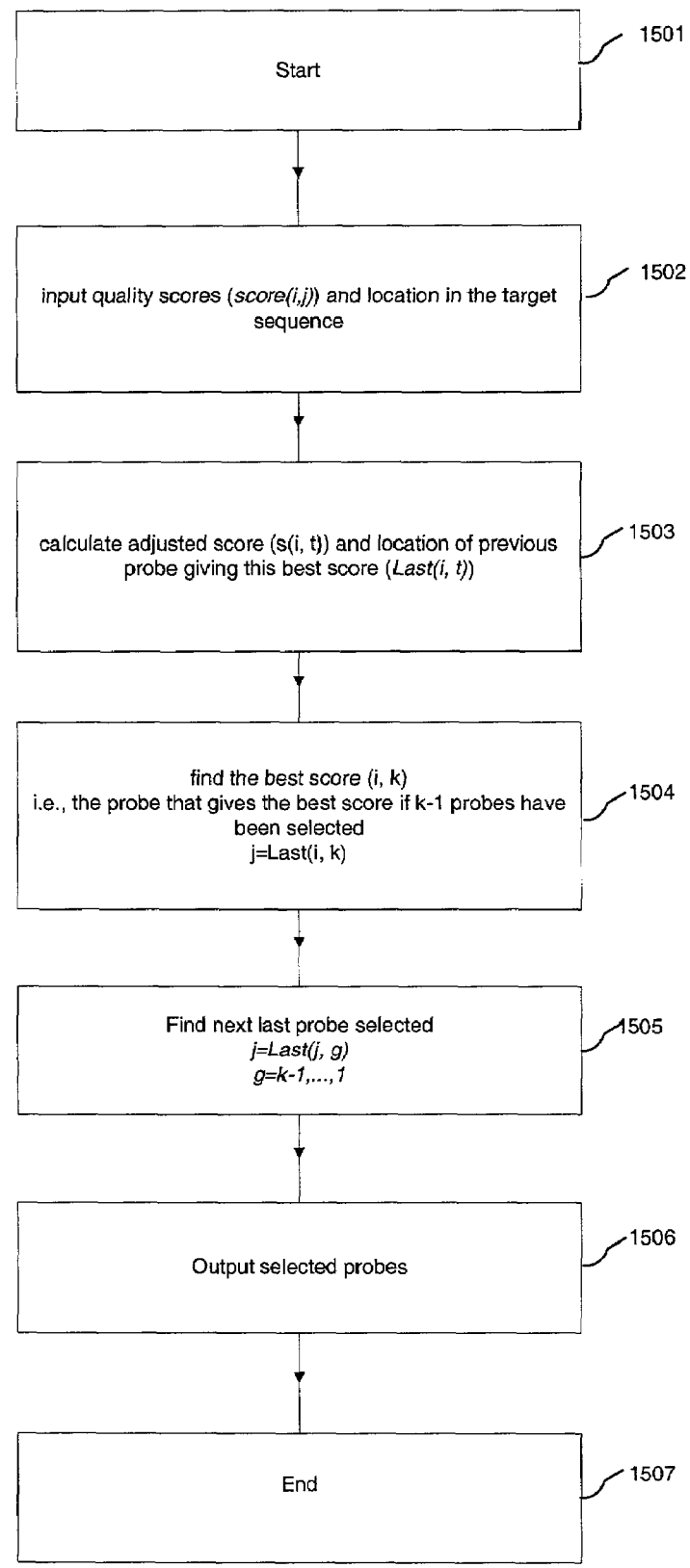
FIG. 15 shows one embodiment of the computer implemented process of the invention.

In some embodiments, dynamic programming is used to select the optimal set of probes with maximum aggregate adjusted scores. FIG. 15 shows an exemplary computer implemented process.

A computer program starts (1501) and inputs (1502) quality scores (score(i)) and location of the probes in the target sequence.

Step 1503 calculates Score(i,t), i.e., best score using probe i last with t−1 probes chosen before i and Last(i,t), i.e., previous location j providing this best score. The following is an exemplary pseudo-code for this process:

```
CalculatingBestScore() {
    //Initializing - the score for the first probe selected
    for (i=1; i<=n; i++){
        Score(i,1) = score(i);
        Last(i,1) = I;
    }
    //running through all scores for selecting additional probes
    for (t=2; t<=k; t++){
        for (i=1; i<=n; i++) {
            Score(i,t)
            = max {j in 1...i-1 Score(j,t−1)=score(i)*Screen
            (position(i)−position(j) }
            Last(i,t)=j; //last (i, j) records where the max occurs
        }
    }
}
```

This algorithm may be accelerated by utilizing the fact that probes that do not overlap have full scores, so not all 'j' have to be searched over.

The best set of k probes given the scores can be found by backtracking through the Score matrix to extract the k probes that together yield the best score (Steps 1504, 1505, 1506, 1507). Step 1504 finds the best score for Score(i,k). The "last" probe selected is probe i. j=Last(i,k) at this location gives us the next-to-last probe selected for the best set (1504). Similarly, Last(j, k−1) gives us the next-to-next-to-last probe (1505).

The following is an exemplary pseudo-code for this process:

```
FindBestProbes() {
    l[0] = bloc;
    //last score added, l[0] is the location of the last probe selected
    i = Last(l[0], k); //i the last probe selected.
    for (g=k−1; g>=1; g--) {
        p = Last(i,g);
        l[k-g] = i;
        i = k;
    }
}
```

In some embodiments, an additive gap score penalty (as opposed to the multiplicative described above) is used, but it seems that the multiplicative penalty provides better results. Particularly preferred embodiments employ dynamic programming to select probes. The dynamic program optimizes the best set of probes, rather than optimizing individual probes. The gap penalty formulation is very flexible, and allows for explicit trade-offs between distance and quality. Because the gap penalty stops changing after a certain distance, the algorithm may be accelerated, and run in time proportional to k*n*(length of penalty), much, much faster than k*n*n without acceleration.

VI. Examples

The following examples demonstrate the effectiveness of the methods of the invention for predicting hybridization intensities and for selecting oligonucleotide probes for gene expression monitoring.

A. Example 1

Prediction of Hybridization Intensities of Probes Against Yeast Genes

Figure 16:
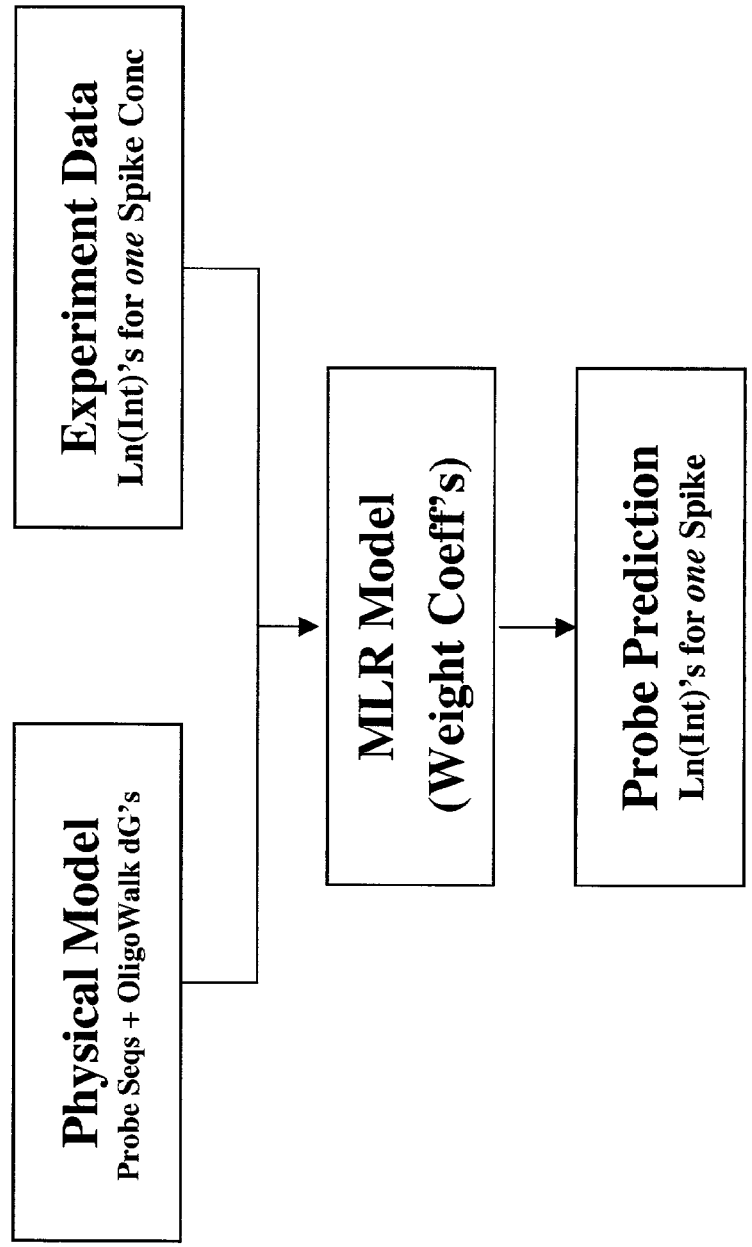
FIG. 16 shows a process for obtaining weight coefficients.

FIG. 16 shows the overall process of the experiments. Yeast was used as a model system for this experiment because the yeast genome had been sequenced. Arrays containing nucleic acid probes complementary to yeast genes are commercially available from Affymetrix (Santa Clara, Calif.). Genes were selected to cover sequence complexity such as GC content, secondary structure, Motif and gene clusters. Twenty probe pairs (perfect match and mismatch probes) were selected to cover the entire sequence of one of the 112 selected yeast genes. The probes are synthesized in situ on glass substrate using photo-directed synthesis method that was disclosed in, for example, U.S. Pat. Nos. 5,384,261, 5,744,305, 5,445,934 and 6,040,138.

One hundred and twelve yeast clones representing the 112 genes were randomly divided into 14 groups (FIG. 17). Labeled targets prepared from these clones were used as spikes for 14 experiments at various concentration levels from 0 pM to 1024 pM. In some experiments, the spikes derived from yeast gene clones were combined with labeled nucleic acid representing human complex background. A 14×14 Latin square design (FIG. 18) was employed. The numbers in the table indicates the concentration used (pM). For each experiment, 14 groups of genes at 14 different concentrations were pooled together and hybridized to an oligonucleotide probe array. For each Latin Square 14 oligonucleotide probe array hybridization experiments were performed. FIG. 19 shows experiments conducted.

Figure 20:
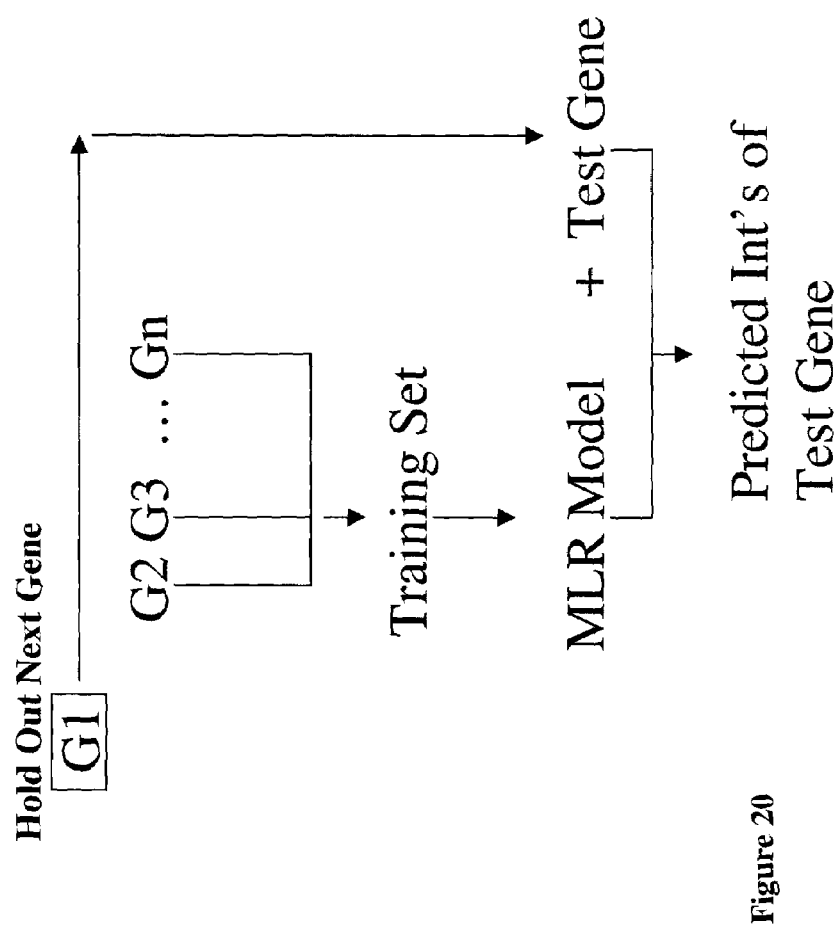
FIG. 20 shows a crossvalidation bootstrapping process.
Figure 21A:
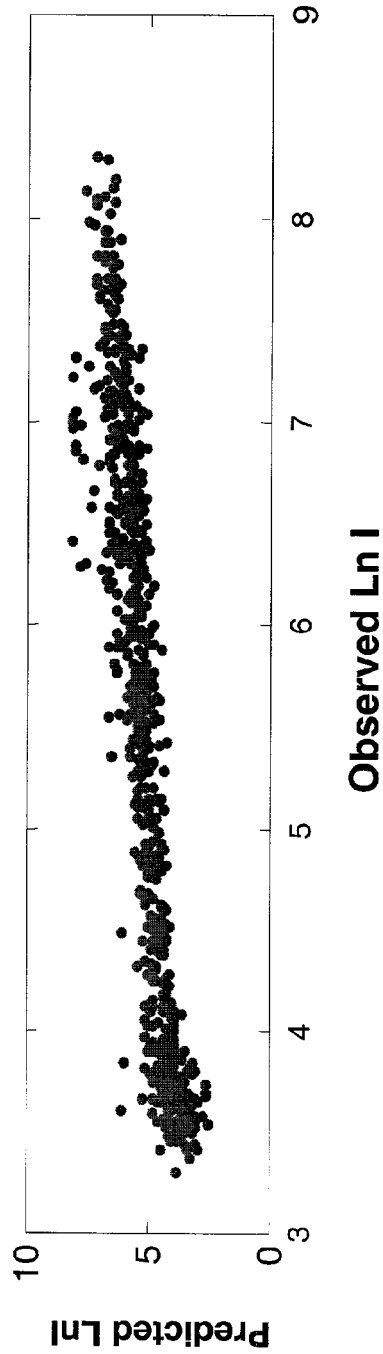
FIGS. 21A, 21B, 22A and 22B show correlation between predicted and observed hybridization intensities for perfect match probes and mismatch probes.
Figure 21B:
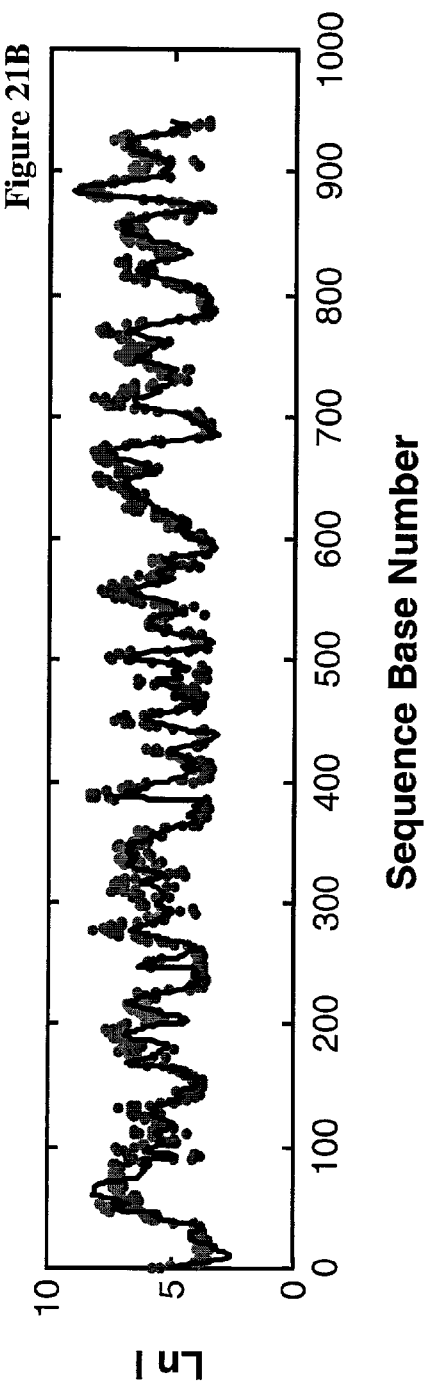
Figure 22A:
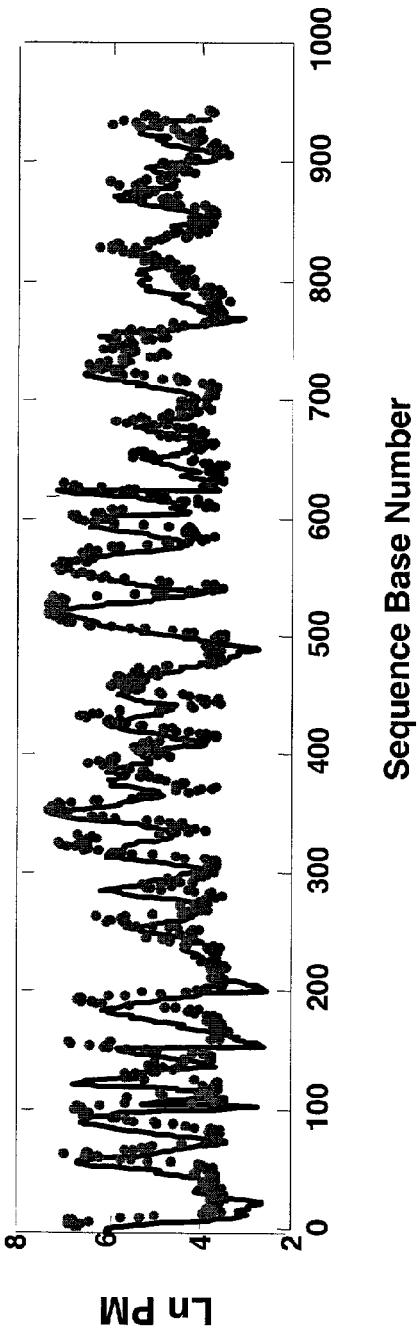
Figure 22B:
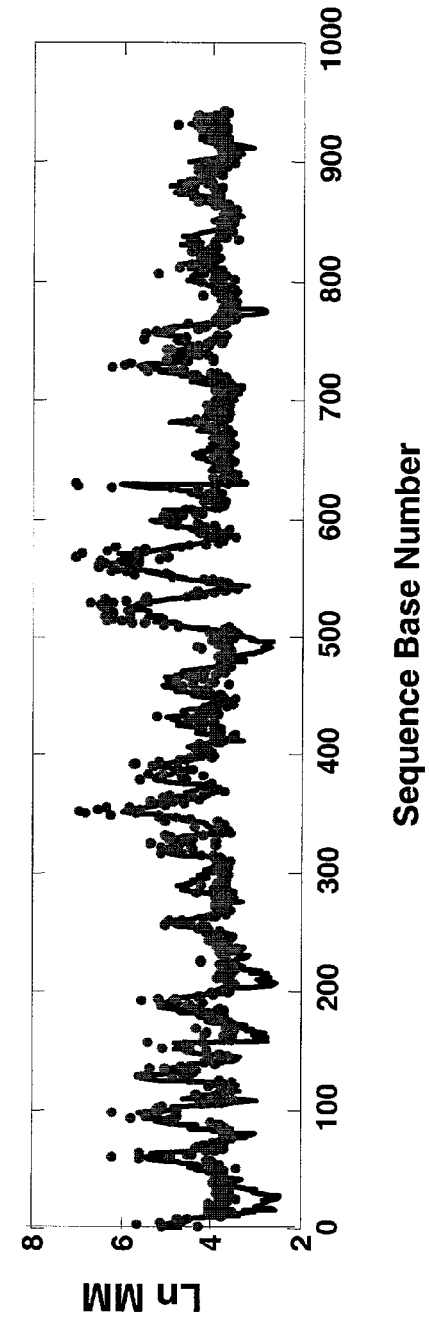

Cross-validation (FIG. 20) was used to evaluate the prediction. The cross-validation process held one gene for test and used the other 111 genes to solve the weight coefficients that in turn were used to predict intensities for the test genes, as described in FIG. 20. The correlation between the predicted and measured intensity for one test gene (YDR113C) is shown in FIG. 21A, and FIG. 21B shows the correlation against target sequence, where lines represent the predicted values and dots represent the observed values. The correlation of the predicted and measured values for perfect match (PM) and mismatch (MM) probes is also demonstrated in FIGS. 22A and 22B respectively, where lines represent the predicted values and dots represent the observed values for gene YGR109C.

Figure 23:
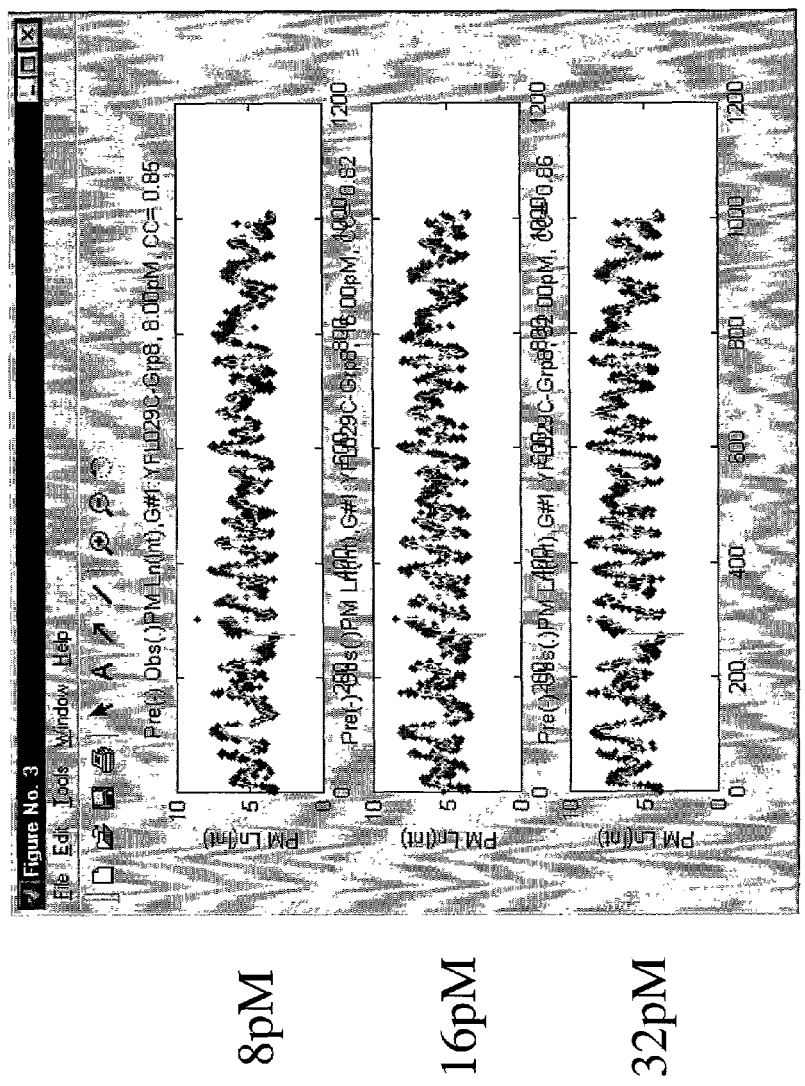
FIG. 23 shows hybridization intensity at different spike concentrations.
Figure 24:
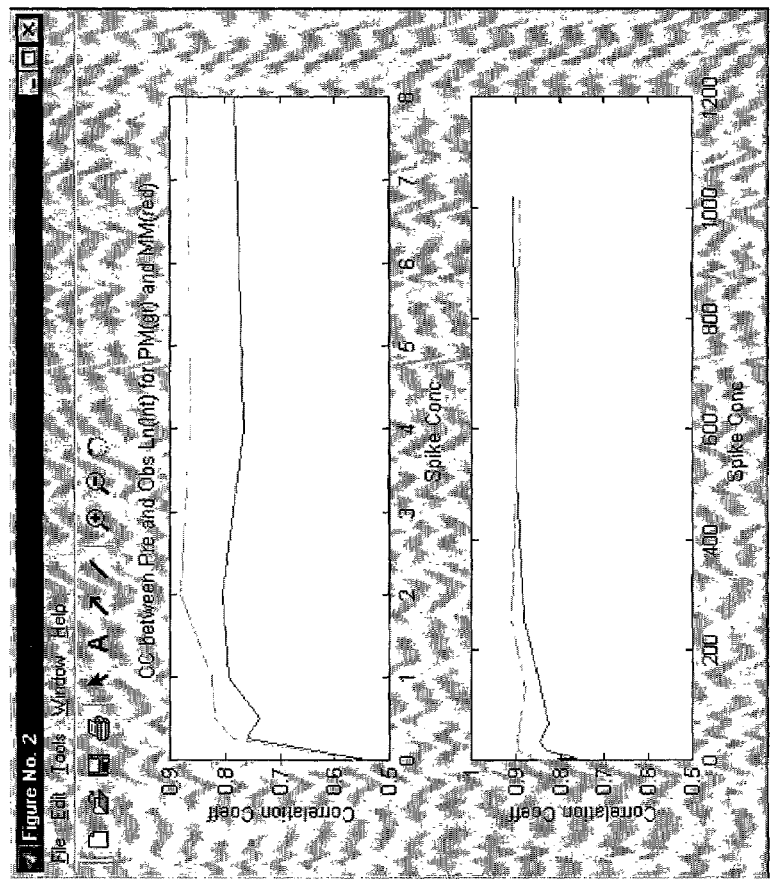
FIG. 24 shows correlation between predicted and observed intensities over the entire concentration range.

FIG. 23 shows predicted intensity versus actual intensity at various target spike concentrations, where lines indicate the predicted values and dots represent observed values. FIG. 24 shows correlation coefficients between predicted and observed intensity (LnI) as function of concentration, where top and bottom lines represent perfect matches and mismatches, respectively. The high correlation (0.85) holds for 4000-fold concentration range (FIG. 24), and the results demonstrate that the methods of invention are able to predict probe behaviors through a wide dynamic range.

Figure 25:
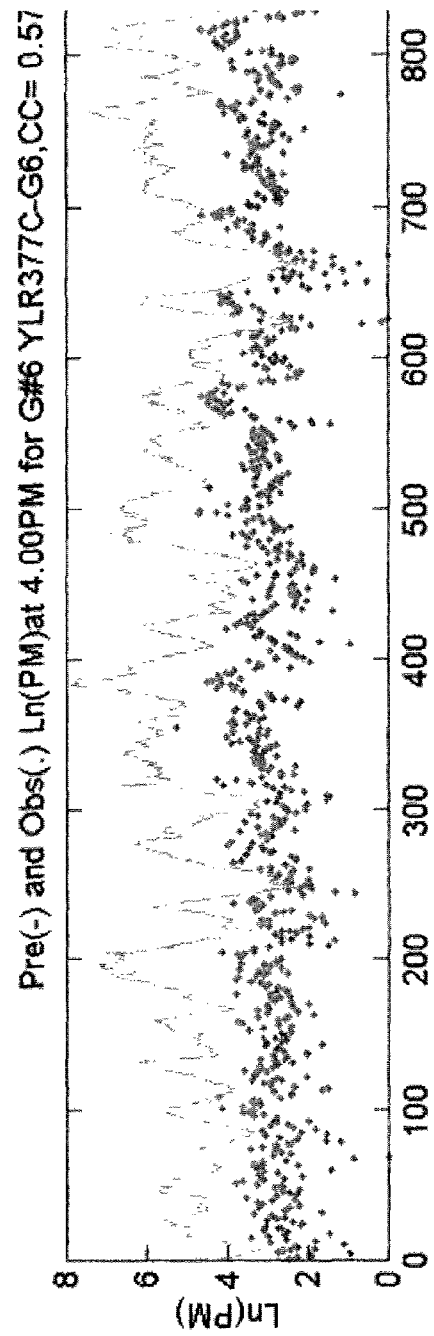
FIG. 25 shows predicted versus observed intensities for negative control target.

FIG. 25 shows predicted versus observed intensities when the target transcripts were derived from genes in the wrong orientation, which resulted in no complimentary target generated for the probes. As shown in FIG. 25, predicted intensities (lines) had no correlation with observed intensity (dots) because right target is absent. The result indicates the prediction method is accurate and specific.

FIG. 26 shows predicted slope versus observed slope. In some regions in FIG. 26 (top), the values of predicted slope (lines) can be quite high when the values of observed slope (dots) because of the saturated probes in those regions.

According to Equation 12 and FIG. 9, the saturated probes can be identified and removed. FIG. 26 (middle) shows the predicted slope profiles after filtering the saturated probes and the significant improvement in the overall correlation after these regions are removed.

B. Example 2

Prediction of Hybridization Intensities of Probes from Human Genes

Figure 27:
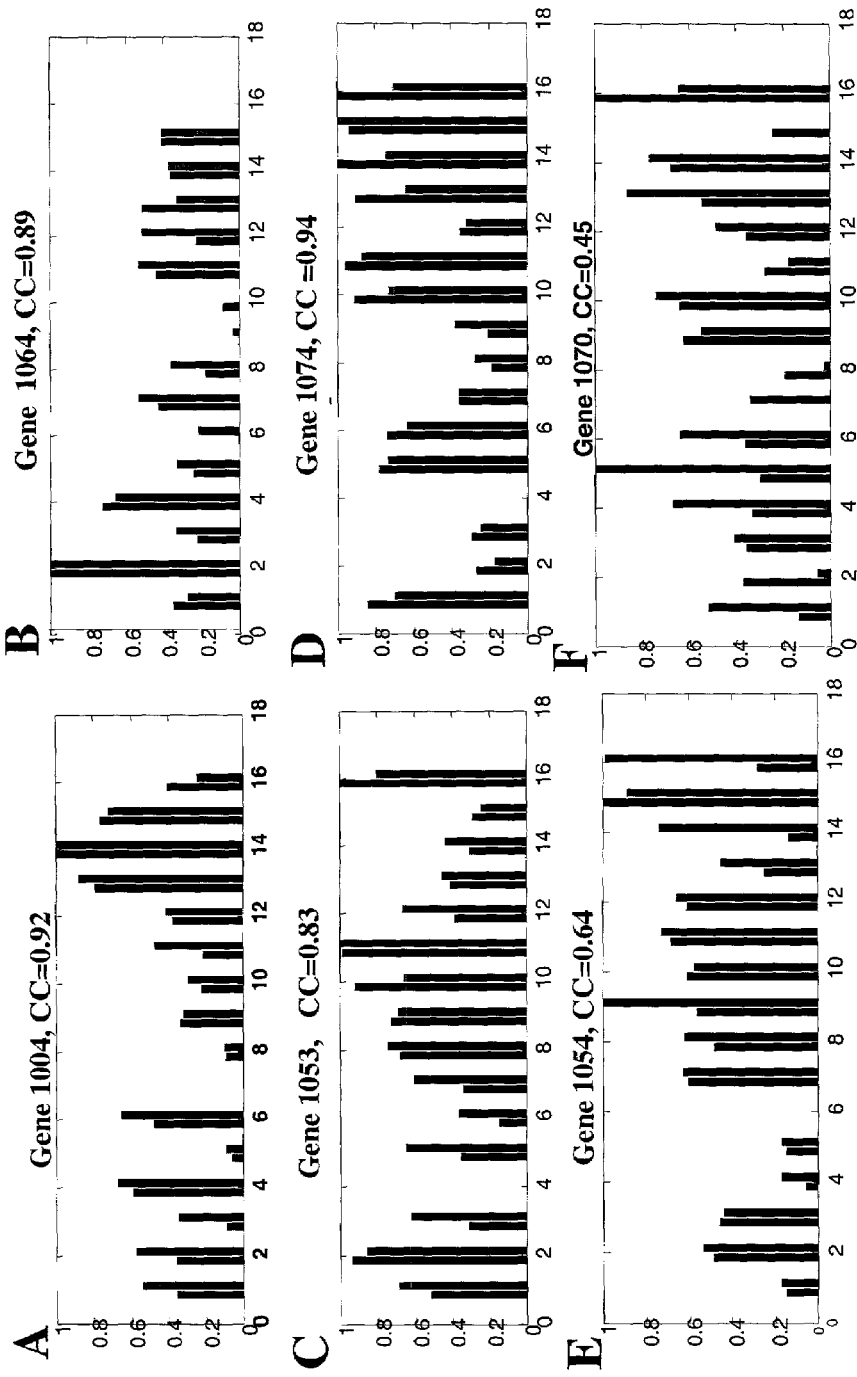
FIG. 27 shows prediction of hybridization of a human expression chip to human target sequences using weight coefficients generated from the yeast model system.
Figure 28:
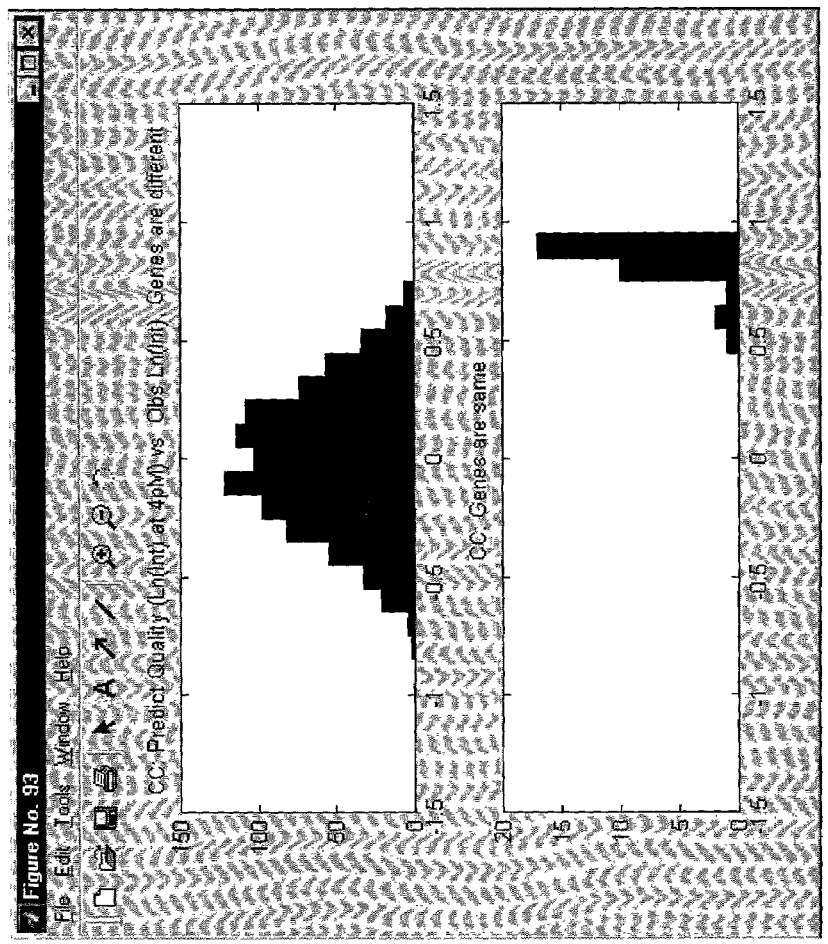
FIG. 28 shows distribution of correlation coefficients.

This example demonstrates that weight coefficients obtained from the model yeast experiment system is also able to predict the intensities on the human gene expression chip and the predicted intensities (left bar) are highly correlated with observed intensities (right bar) at each probe position as indicated by x-axis. The correlation is shown in FIGS. 27 A–E. Typically, the correlation coefficients ranged from 0.45–0.83. The distribution of the correlation coefficients are shown in FIG. 28. These results demonstrate that the probe selection model may be generalized to different organisms such as mammals, plants.

C. Example 3

Probe Selection

Figure 29:
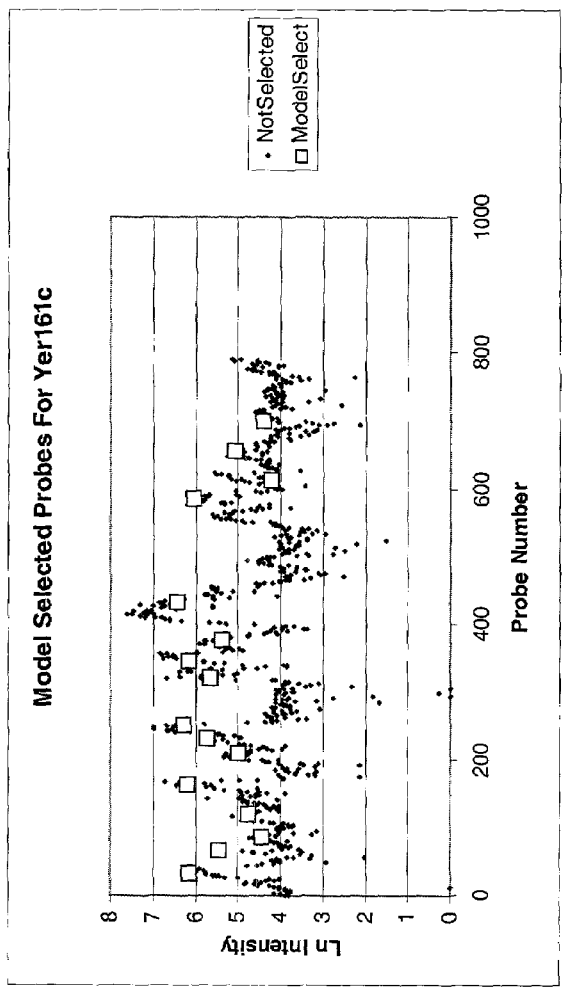
FIG. 29 shows selection of probes using dynamic programming.
Figure 30:
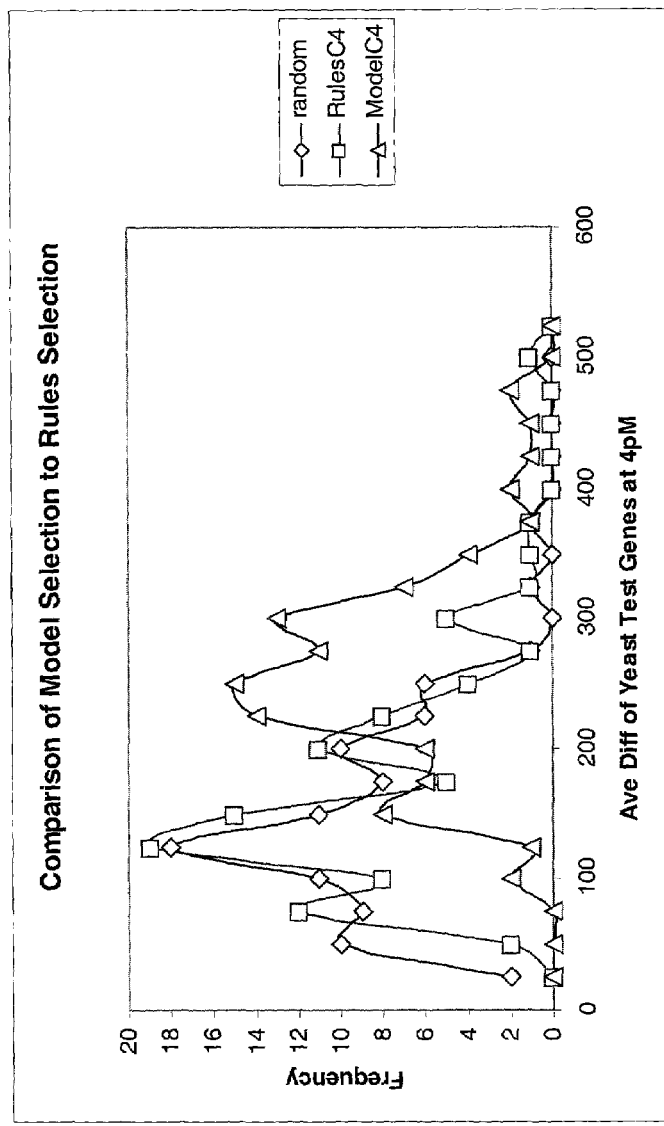
FIG. 30 compares different methods for selecting probes.

This example demonstrates that the model-based probe selection method and software may provide improvement over current probe selection methods. FIG. 29 shows intensity values of sixteen probes (open squares) selected for the Ycr161c gene based upon quality scores and using dynamic programming. FIG. 29 also shows that the sixteen selected probes (open squares) are spaced along sequence. FIG. 30 shows a comparison of average intensity difference (between perfect match and mismatch) values of probe selected by various methods for all yeast test genes. Probes selected randomly (diamonds) were similar to those selected according empirical rules (squares). The model based selection method (triangles) improved average intensity difference values. The result indicates the model-selected probes have high sensitivity and specificity.

CONCLUSION

The present invention provides methods and computer software products for predicting nucleic acid hybridization affinity, detecting mutation, selecting better-behaved probes, and improving probe array manufacturing quality control. It is to be understood that the above description is intended to be illustrative and not restrictive. Many variations of the invention will be apparent to those of skill in the art upon reviewing the above description. By way of example, the invention has been described primarily with reference to the design of a high density oligonucleotide array, but it will be readily recognized by those of skill in the art that the methods may be used to predict the hybridization affinity of other immobilized probes, such as probes that are immobilized in or on optical fibers or other supports by any deposition methods. The basic methods and computer software of the invention may also be used to predict solution-based hybridization. The scope of the invention should, therefore, be determined with reference to the appended claims, along with the full scope of equivalents to which such claims are entitled. All references cited herein are incorporated herein by reference for all purposes.

What is claimed is:

1. A computer implemented method for selecting nucleic acid probes comprising:
    inputting quality scores and locations for a plurality (n) of candidate probes;
    selecting k number of probes from the n number of candidate probes, wherein the selected probes have a maximum aggregate adjusted quality score; wherein the adjusted quality score is based upon the quality score and a penalty for the overlapping of the selected probes; and
    outputting the selected probes.

2. The method of claim 1 wherein the adjusted quality score is calculated according to:

$$S' = S\sqrt{\frac{(l-o)}{l}},$$

wherein S' is an adjusted quality score; S is the initial quality score; l is the probe length, and o is the overlap the probe has with other probes.

3. The method of claim 2 wherein k is greater than 3.
4. The method of claim 3 wherein k is greater than 5.
5. The method of claim 4 wherein k is greater than 10.
6. The method of claim 5 wherein k is greater than 15.
7. The method of claim 2 wherein the selecting step comprises performing dynamic programming optimization on the n number of candidate probes to adjust their quality scores to the extent of overlap between them to obtain an optimal k number of probes with optimal aggregate adjusted quality scores.

8. The method of claim 7 wherein the selecting comprises steps of:
    calculating best adjusted quality scores (Sccre(i,t) for probe i last with t−1 probes chosen before i and previous location j providing this best score (Last(i,k));
    determining the best adjusted quality scores for Score(j, k) to select the last probe; and
    selecting the next probe according to Last(the probe selected, number of probes remaining to be selected); and
    repeating the selecting step until all k probes are selected.

9. A system for selecting nucleic acid probes comprising:
    a processor; and
    a memory coupled with the processor, the memory storing a plurality of machine instructions that cause the processor to perform logical steps, wherein the logical steps include:
    inputting quality scores and locations for a plurality (n) of candidate probes;
    selecting k number of probes from the n number of candidate probes, wherein the selected probes have a maximum aggregate adjusted quality score; wherein the adjusted quality score is based upon the quality score and a penalty for the overlapping of the selected probes; and
    outputting the selected probes.

10. The system of claim 9 wherein the adjusted quality score is calculated according to:

$$S' = S\sqrt{\frac{(l-o)}{l}},$$

wherein S' is an adjusted quality score; S is a quality score; l is the probe length, o is the overlap the probe has with other probes.

11. The system of claim 10 wherein k is greater than 3.
12. The system of claim 11 wherein k is greater than 5.
13. The system of claim 12 wherein k is greater than 10.
14. The system of claim 13 wherein k is greater than 15.
15. The system of claim 14 wherein the selecting step comprises performing dynamic programming optimization on the n number of candidate probes to adjust their quality scores to the extent of overlap between them to obtain an optimal k number of probes with optimal aggregate adjusted quality scores.
16. The system of claim 15 wherein the selecting comprises steps of:
  calculating best adjusted quality scores (Score(i,t)) for probe i last wit t−1 probes chosen before i and previous location j providing this best score (Last(i,k));
  determining the best adjusted quality scores for Score(j, k) to select the last probe; and
  selecting the next probe according to Last(the probe selected, number of probes remain to be selected); and
  repeating the selecting step until all k probes are selected.
17. A computer readable medium having computer executable instructions for performing a method comprising:
  inputting quality scores and locations for a plurality (n) of candidate probes;
  selecting k number of probes from the n number of candidate probes, wherein the selected probes have a maximum aggregate adjusted quality score;
  wherein the adjusted quality score is based upon the quality score and a penalty for the overlapping of the selected probes; and
  outputting the selected probes.
18. The computer readable medium of claim 17 wherein the adjusted quality score is calculated according to:

$$S' = S\sqrt{\frac{(l-o)}{l}},$$

wherein S' is an adjusted quality score; S is a quality score; l is the probe length, o is the overlap the probe has with other probes.

19. The computer readable medium of claim 18 wherein k is greater than 3.
20. The computer readable medium of claim 19 wherein k is greater than 5.
21. The computer readable medium of claim 20 wherein k is greater than 10.
22. The computer readable medium of claim 21 wherein k is greater than 15.
23. The computer readable medium of claim 22 wherein the selecting step comprises performing dynamic programming optimization on the n number of candidate probes to adjust their quality scores to the extent of overlap between them to obtain an optimal k number of probes with optimal aggregate adjusted quality scores.
24. The computer readable medium of claim 23 wherein the selecting comprises steps of:
  calculating best adjusted quality scores (Score(i,t)) for probe i last with t−1 probes chosen before i and previous location j providing this best score (Last(i,k));
  determining the best adjusted quality scores for Score(j, k) to select the last probe; and
  selecting the next probe according to Last(the probe selected, number of probes remain to be selected); and
  repeating the selecting step until all k probes are selected.
25. A computer implemented method for selecting nucleic acid probes comprising:
  inputting quality scores and locations for a plurality (n) of candidate probes;
  selecting k number of probes from the n number of candidate probes, wherein the selected probes have a maximum aggregate adjusted quality score; wherein the adjusted quality score is based upon the quality score and a penalty for the overlapping of the selected probes; and
  outputting the selected probes, wherein the outputting of the selected probe sequences is to a file.
26. A system for selecting nucleic acid probes comprising:
  a processor; and
  a memory coupled with the processor, the memory storing a plurality of machine instructions that cause the processor to perform logical steps, wherein the logical steps include:
  inputting quality scores and locations for a plurality (n) of candidate probes;
  selecting k number of probes from the n number of candidate probes, wherein the selected probes have a maximum aggregate adjusted quality score; wherein the adjusted quality score is based upon the quality score and a penalty for the overlapping of the selected probes; and
  outputting the selected probes, wherein the outputting of the selected probe sequences is to a file.
27. A computer readable medium having computer executable instructions for performing a method comprising:
  inputting quality scores and locations for a plurality (n) of candidate probes;
  selecting k number of probes from the n number of candidate probes, wherein the selected probes have a maximum aggregate adjusted quality score;
  wherein the adjusted quality score is based upon the quality score and a penalty for the overlapping of the selected probes; and
  outputting the selected probes, wherein the outputting of the selected probe sequences is to a file.

* * * * *